United States Patent
Tang et al.

(10) Patent No.: US 12,049,525 B2
(45) Date of Patent: Jul. 30, 2024

(54) RADIOPAQUE POLYMERS

(71) Applicant: BIOCOMPATIBLES UK LIMITED, Surrey (GB)

(72) Inventors: Yiqing Tang, Guildford (GB); Andrew Lennard Lewis, Farnham (GB); Jonathan Vince, Hampshire (GB); Hugh Britton, Gillingham (GB); Koorosh Ashrafi, Purley (GB); Damien Guegan, Fontaine (FR); Sean Leo Willis, Farnham (GB)

(73) Assignee: Boston Scientific Medical Device Limited, Galway (IE)

( * ) Notice: Subject to any disclaimer, the term of this patent is extended or adjusted under 35 U.S.C. 154(b) by 818 days.

(21) Appl. No.: 17/252,552

(22) PCT Filed: Jun. 26, 2019

(86) PCT No.: PCT/IB2019/055392
§ 371 (c)(1),
(2) Date: Dec. 15, 2020

(87) PCT Pub. No.: WO2020/003152
PCT Pub. Date: Jan. 2, 2020

(65) Prior Publication Data
US 2021/0115171 A1  Apr. 22, 2021

(30) Foreign Application Priority Data

Jun. 29, 2018 (GB) ..................... 1810788

(51) Int. Cl.
| | | |
|---|---|---|
| *C08F 16/06* | (2006.01) | |
| *A61K 49/04* | (2006.01) | |
| *C08F 8/18* | (2006.01) | |
| *C08J 3/075* | (2006.01) | |
| *C08J 3/12* | (2006.01) | |
| *C08J 3/24* | (2006.01) | |

(52) U.S. Cl.
CPC .......... *C08F 16/06* (2013.01); *A61K 49/0442* (2013.01); *A61K 49/048* (2013.01); *C08F 8/18* (2013.01); *C08J 3/075* (2013.01); *C08J 3/12* (2013.01); *C08J 3/24* (2013.01)

(58) Field of Classification Search
CPC ....... A61K 9/5026; A61K 9/5021; C08J 3/24; C08J 3/075; C08F 16/06
See application file for complete search history.

(56) References Cited

U.S. PATENT DOCUMENTS 6,699,920 B1   3/2004   Andros

FOREIGN PATENT DOCUMENTS

| CN | 102007192 A | 4/2011 | |
| CN | 103687902 A | 3/2014 | |
| CN | 105517582 A | 4/2016 | |
| CN | 107523253 A | 12/2017 | |
| DE | 480866 C | 8/1929 | |
| JP | 2018145328 A | 9/2018 | |
| WO | WO-2014106830 A1 * | 7/2014 | ............. A01N 37/18 |

OTHER PUBLICATIONS

Machine translation of WO 2014106830 (Year: 2023).*
Wahit et al., "Poly-based biodegradable polyesters: a short review" Reviews in Chemical Engineering-2015-22 pages.
Yamaoka et al., Comparison of Body Distribution of Poly(vinyl alcohol) with Other Water-soluble Polymers After Intravenous Administration-J. Pharm. Pharmacol. 1995, 47: 479-486.
Avila-Salas et al., "In-Silico Design, Synthesis and Evaluation of a Nanostructured Hydrogel as a Dimethoate Removal Agent" Nanomaterials, vol. 8, Issue 1, p. 1-14, published on Jan. 4, 2018. Switzerland.
Mazumdar Nasreen et al., ""Iodine complexes of acid-functionalized poly(vinyl alcohol) hydrogels: synthesis, characterization and release studies"", Journal of Polymer Materials, New, Delhi, India, vol. 33, No. 1, 2016, p. 41-52.
International Search Report and Written Opinion for the InternationalPatent Application No. PCT/IB2019/055392, mailed Jun. 29, 2020, 19 pages.

* cited by examiner

Primary Examiner — James W Rogers
(74) Attorney, Agent, or Firm — Seager, Tufte & Wickhem, LLP

(57)  ABSTRACT

A polymer having a backbone comprising a polyhydroxylated polymer cross linked by a C3 to C8 diacid.

15 Claims, 4 Drawing Sheets

A

B

C

RADIOPAQUE POLYMERS

CROSS-REFERENCE TO RELATED APPLICATION

This is the United States National Phase entry of International Application No. PCT/IB2019/055392, filed Jun. 26, 2019, which claims priority to Great Britain Application No. 1810788.8, filed Jun. 29, 2018, the disclosures of which are incorporated herein by reference in their entireties.

This invention relates to polymers, and particularly to degradable polymers, to medical devices comprising these polymers and to methods of medical treatment using the devices and polymers. The invention particularly relates to degradable microspheres.

Therapeutic embolisation is a minimally invasive procedure in which a material is introduced into a blood vessel to produce an occlusion in order to slow or stop blood flow. Typically, such materials are delivered via a catheter, which is navigated to the target site from a peripheral point such as the leg or wrist. This approach has been useful in the treatment of conditions such as gastrointestinal bleeding, arteriovenous and malformations, hyper vascular malignant tumours such as hepatocellular carcinoma, benign growths such as uterine fibroids and more recently benign prostate hyperplasia (BPH) amongst others.

Biocompatible microspheres are useful embolic agents because they can be easily delivered to the target site and can be provided in defined size ranges for more predictable embolization according to the vessel size.

A variety of degradable microspheres has been proposed. These may be based on naturally occurring polymers such as albumin, gelatin, chitosan or starch. However such polymers may provoke reactive responses in humans due to sensitivities to the polymer themselves or to contaminants. Some natural polymers derived from animal sources require careful control of contaminants such as viruses, or may have naturally occurring variability leading to potential source-to-source variability in the polymer and its properties.

Synthetic polymers have also been proposed. Amongst the most widely used synthetic biodegradable polymers are polyesters, such as polylactides, polyglycolides or co-polymers of these such as poly lactide co-glycolides. These polymers are typically solid and rigid having poor compressibility, which can lead to catheter clogging, when used to make microspheres. Although these materials can be made to incorporate drugs, for example by mixing the drug into the polymer during manufacture, this is typically limited to lipophilic drugs or to solid formulations, due to the hydrophobic nature of the material. Further, since the polymer is typically monolithic, release of the drug is governed by degradation of the polymer and so may be relatively slow. It is also difficult to remove solvent residue from the material post synthesis and so traces may remain in the material.

A further disadvantage of synthetic biodegradable polymers is that the breakdown products must be extensively characterised for safety and clearance from the body, making development long and costly.

The inventors have identified that one or more of the above issues can be addressed by the polymers of the present invention.

In a first aspect the present invention therefore provides a polymer having a backbone comprising a polyhydroxylated polymer the polyhydroxylated polymer cross-linked by a C3 to C8 dicarboxylic acid. This aspect also provides a polymer obtainable by crosslinking a polymer having a polyhydroxylated polymer backbone with a C3 to C8 dicarboxylic acid.

The polyhydroxylated polymer is a polymer that comprises repeating units bearing one or more pendant hydroxyls. Preferred polyhydroxylated polymers include those comprising polyol esters of acrylates and methacylates, poly(hydroxyalkylacrylates) and poly(hydroxyalkylmethacrylates), such as poly(hydroxyethyl methacrylate); poly (hydroxyalkylacrylamides) and poly(hydroxyalkyl methacrylamides), such as Trishydroxymethylmethacrylamide; poly(PEG acrylates) and poly(PEG methacrylates), polymers comprising vinylalcohols such as poly(vinylalcohol) or (ethylene-vinylalcohol) copolymers; and polysaccharides such as starches, chitosans, glycogens, celluloses, such as methyl celluloses, alginates, and polysaccharide gums, such as carageenans, guars, xanthans, gellans, locus bean gums and gum arabics.

Particularly preferred polymers are those comprising 1,2-diol or 1,3-diol groups and more preferably those comprising vinylalcohols such as poly(vinylalcohol) (PVA) or ethylene-vinylalcohol (EtVA) polymers and copolymers. Most preferably the polymer is a PVA homopolymer or copolymer, or a polysaccharide.

The PVA preferably has a weight average molecular weight (MW) of between 2000 and 180,000, or 200,000 Da and, particularly between 2000 or 3000 and 67,000. PVA polymers having a weight average molecular weight 67,000 Da or less are preferred as PVA in this weight range is capable of being rapidly cleared from the body, particularly via kidney excretion. More preferably the PVA has a weight average molecular weight (MW) of 2000 to 32,000 or 10,000 to 32,000.

Biodegradable polymers herein have linkages that are cleaved by hydrolysis within the body, such that the polymer breaks down. The period over which the polymer degrades can be tuned by altering parameters such as the average molecular weight of the backbone, the molar ratio of backbone to cross linker and the species of cross linker as demonstrated further herein. The preferred polymers degrade to soluble components over a period of 1 hour to 1 year.

The polyhydroxylated polymer may be cross linked by a variety of C3, C4, C5, C6, C7 or C8 diacids, preferably C3 to C6 diacids. These diacids may be, for example, a C3, C4, C5, C6, C7 or C8 saturated diacid, mono unsaturated diacid, and in the case of C6 C7 and C8 unsaturated diacid, a diunsaturated acid. In each case, unbranched acids are preferred.

Where the polymer is cross linked by a C3 to C8 saturated diacid, this is preferably selected from malonic, succinic and glutaric acids.

The saturated diacid may be substituted by a group selected from —OH, =O and —NH$_2$. Where the acid is substituted by a ketone, it is preferably a C4, C5, C6, C7 or C8 alpha keto acid, preferably alpha ketoglutarate. Alternatively the alpha keto acid is oxaloacetate. Where the acid is substituted by an amino group, it is preferably aspartic or glutamic acid. Polymers in which polymers comprising PVA are cross linked by such diacids are one preferred embodiment.

Where the polymer is cross linked by a C4 to C8 unsaturated diacid, this is preferably selected from maleic, fumaric or cis or trans galaconic acids, the trans isomer being preferred.

In all cases, it is preferred that the cross linking diacid is naturally occurring in the human body, since such compounds are easily metabolised and/or cleared from the body. Examples of such acids include, but are not limited to, malonic, succinic, glutaric, fumaric, glutaconic, malic, aspartic, glutamic, oxaloacetate, and alpha ketoglutarate.

In one embodiment of the invention, the polymer comprises groups of the formula 1:

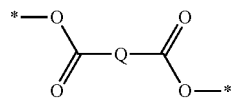

1 wherein

*is the point of attachment to the polyhydroxylated polymer via the ester group; and wherein Q is a group of the formula 1a:

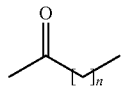

1a wherein n is 1 to 5, preferably 1 to 3; more preferably 1 or 2;

or Q is a $C_{1-6}$ alkylene or $C_{2-6}$ alkenylene group; preferably a $C_{1-4}$ alkylene or $C_{2-4}$ alkenylene group; wherein alkylene groups are optionally substituted by —OH or —NH$_2$. Single substitutions are preferred.

In a further embodiment the invention provides a polymer obtainable by cross-linking a polymer comprising a polyhydroxylated polymer with a compound of the formula II wherein ester links are formed between the polyhydroxylated polymer and the compound of the formula 2;

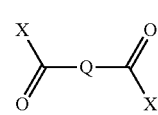

2 wherein X is —OH or a suitable leaving group and wherein the leaving group is selected from imidazolyl, mesylate, tosylate, —O-alkyl, such as —O—($C_{1-6}$)alkyl, chloride, bromide, fluoride and —O-acyl such as such as —O—($C_{1-6}$)acyl groups.

Where X is —OH, the oxygen may be activated by the use of an activating agent such as DCC (N,N'-dicyclohexylcarbodiimide), EDCI (N-(3-dimethylaminopropyl)-N'-ethylcarbodiimide) and HOBt (hydroxybenzotrazole).

The reaction is typically carried out in a polar aprotic solvent such as 1-methyl-2-pyrrolidinone (NMP), DMF or DMSO mixtures thereof. The reaction may be carried out at an elevated temperature, ie, greater than 20° C.

Where the polymer backbone is or comprises PVA, such as PVA homopolymers and co-polymers, the polymer comprises cross linking groups of formula 3 which cross link the PVA

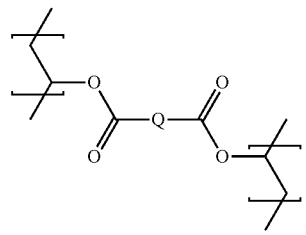

3

A second aspect of the invention provides a method of making a biodegradable polymer comprising cross-linking polyhydroxylated polymer with a compound of formula 2 to form ester linkages between the polyhydroxylated polymer and the compound of the formula 2 thereby cross linking the polymer;

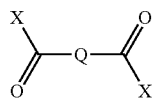

2 wherein X is —OH or a suitable leaving group. The leaving group may be selected from imidazolyl, mesylate, tosylate, —O-alkyl, such as —O—($C_{1-6}$)alkyl chloride, bromide, fluoride and —O-acyl groups, such as —O—($C_{1-6}$)-acyl as described above.

In a particularly preferred embodiment, the polymer is a polymer comprising PVA (such as a PVA homopolymer or co-polymer) which is cross linked by alpha-ketoglutarate.

The polymer may be endowed with a variety of functionalities. These include drug elution, either through physical incorporation of the drug into the polymer, or by coupling of the drug to charged groups of the polymer; radioactivity, such as by incorporation of radioactive isotopes into the polymer (e.g. as a powder), by coupling moieties comprising the isotopes to the polymer, such as compounds containing radioactive atomsor by binding the radioisotope to the polymer through ionic interaction, (such as via a charged group on the polymer or through attachement to a chelating group bound to the polymer). Additionally, imageability may be provided through incorporation of imageable species into the polymer (e.g. as a powder), by coupling moieties comprising the imageable species to the polymer or by binding the imageable species to the polymer through ionic interaction, (such as via a charged group on the polymer or through attachement to a chelating group bound to the polymer).

Imageable species render the polymer visible by a medical imaging modality such as X-Ray, positron emission imagining, (PET), or single photon emission computed tomography (SPECT) and MRI.

XRay imageable species include, for example, iodine, barium and tantalum.

Positron emission imaging species include $^{18}$F (which may be incorporated for example as $^{18}$F-fluorodeoxyglucose and coupled to the polymer). SPECT imageable species include thallium-201, technetium-99m, iodine-123, and gallium-67.

MRI imageable species include gadolinium, iron (particularly as superparamagnetic iron oxide particles), platinum and manganese.

The imageable species may be coupled to the polymer (such as by covalent bond, ionic interaction or by chelation) or it may be physically incorporated into the polymer, for example as a powder (e.g. metal particles such as iron or tantalum or powdered compounds such as barium sulphate).

The polymer may also be imageable by echography (for example by the provision of voids or gas bubbles within the polymer).

The polyhydroxylated polymers described herein may be modified by the provision of pendant groups on the polyhydroxylated backbone, to provide one or more functionalities such as imagability, chelation, or ionic binding of drugs. Such pendant groups may be coupled to the backbone through one or more of the hydroxyl groups. Pendant groups may be coupled through ether, ester, carbonate, carbamate or cyclic acetal groups such as 1,3 dioxolone, and 1,3 dioxane groups.

Such pendant moieties may be coupled to the backbone prior to the cross linking or afterwards. Coupling through a single hydroxyl is preferred in coupling to pre-formed crosslinked polymer since it avoids the possibility of unintended additional cross links, for example where the pendant group is linked through more than one hydroxyl of the hydroxylated polymer backbone.

In one embodiment, pendant groups may carry positive or negative charges, which are able to reversibly bind compounds, such as drugs, carrying the opposite charge at physiological pH (pH7.4). A variety of charged species may be used, including sulphonate, phosphate, ammonium, phosphonium and carboxylate groups; carboxylate and sulphonate are preferred.

Example charged groups include $C_{1-6}$ branched or unbranched alkyl groups, $C_{2-6}$ branched or unbranched alkenyl groups or $C_{5-7}$aryl or heteroaryl groups (preferably phenyl or benzyl) each independently substituted by 1 to 3 groups selected from —COOH, —OPO$_3$H$_2$ and —SO$_3$H. Of these groups $C_{1-6}$ branched or unbranched alkyl groups and $C_{2-6}$ branched or unbranched alkenyl groups bearing 1 to 3 carboxylate or sulphonate groups are preferred.

Such groups may be coupled to the polymer backbone through a linker, X, analogously to that detailed below, or, preferably may be directly bonded to the polymer backbone.

Charged groups may be coupled to the polymer backbone through one or more of the hydroxyl groups, but preferably through a single group, particularly if coupled to the polymer after it has been cross linked. As for other pendant groups, suitable coupling groups include ether, ester, carbonate, carbamate or cyclic acetal groups such as 1,3 dioxolone, and 1,3 dioxane groups. Preferred coupling groups are ether, ester, and 1,3 dioxane groups. Ether and ester being preferred, particularly if used to couple the pendant group post cross linking.

Possible pendant groups also include groups comprising one or more, such as 2, 3 or 4, covalently attached iodines; preferably such groups comprise an iodinated aromatic group, having 2, 3 or 4 iodines covalently attached to an aromatic ring, such as a phenyl ring or benzyl group. In one preferred approach, the polymer comprises phenyl groups bearing 2 to 4 covalently bound iodines. Iodine may be the sole substituent of such rings or the phenyl groups may additionally comprise one or two groups, W which are described further below. Such groups may also be coupled to the polymer backbone through coupling groups such as ether, ester, amide, carbonate, carbamate, 1,3 dioxolone, and 1,3 dioxane groups and particularly ether, ester, and 1,3 dioxane groups as also described further below. Ether and ester being preferred particularly if used post cross linking.

Iodine containing pendant groups serve to provide radiopacity to the polymer. Such groups may be coupled to the polymer backbone through a linker, X, as detailed below, or may be directly bonded to the polymer backbone.

In one embodiment, the iodinated pendant groups may be groups of the formula 4a or 4b

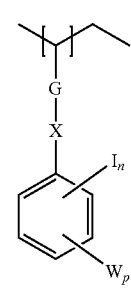

4a

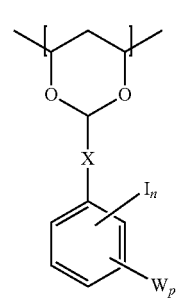

4b

W is independently selected from —OH, —COOH, —SO$_3$H, —OPO$_3$H$_2$, —O—(C$_{1-4}$alkyl), —O—(C$_{1-4}$alkyl) OH, —O—(C$_{1-4}$alkyl)R$^2$, —O—(C$_2$H$_5$O)$_q$R$^1$ —(C═O)—O—C$_{1-4}$alkyl and —O—(C═O)C$_{1-4}$alkyl; or, alternatively W may be a zwitterionic group of the formula —BZ, although such —BZ groups are less preferred;

wherein —OH, COOH, —OPO$_3$H$_2$ and —SO$_3$H maybe in the form of a pharmaceutically acceptable salt;

X is either a bond or a linking group having 1 to 8 carbons and optionally 1 to 4 heteroatoms selected from O, N and S; although S is less preferred.

G is a coupling group through which the group of the formula I is coupled to the polymer and is selected from ether, ester, amide, carbonate, carbamate, 1,3 dioxolone, and 1,3 dioxane; particularly ether, ester, amide, carbonate, carbamate, and most particularly ether or ester. R$^1$ is H or Ch$_{1-4}$ alkyl;

R$^2$ is —COOH, —SO$_3$H, or —OPO$_3$H$_2$; preferably —COOH or —SO$_3$H, q is an integer from 1 to 4;

n is an integer from 1 to 4; preferably 2 or 3 p is 0, 1 or 2; preferably 1 or 2; and wherein —COOH, —OPO$_3$H$_2$ and —SO$_3$H as well as phenolic —OH maybe in the form of a pharmaceutically acceptable salt;

Where W is a zwitterionic group of formula —BZ: B is a bond, or a straight branched alkanediyl, oxyalkylene, alkylene oxaalkylene, or alkylene (oligooxalkylene) group, optionally containing one or more fluorine substituents; and Z is a zwitterionic ammonium, phosphonium, or sulphonium phosphate or phosphonate ester group.

The group Z is zwitterionic and comprises, as the cationic moiety, an ammonium, phosphonium or sulphonium group. Preferably the cation is an ammonium group. The anion of the zwitterion is a phospho moiety. It is generally a phosphate diester, or a phosphonate ester based moiety.

Generally in Z, the anion is closer to B than the cation (non phosphobetaines). However in some zwitterions, the cation is closer to the group B than is the anion (called hereinafter phosphobetaines).

Preferably in non phosphobetaines, Z is a group of the general formula 5.

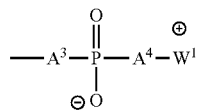

5 in which the moieties $A^3$ and $A^4$, which are the same or different, are —O—, —S—, —NH— or a valence bond; preferably —O—, and $W^+$ is a group comprising an ammonium, phosphonium or sulphonium cationic group and a group linking the anionic and cationic moieties which is preferably a $C_{1-12}$alkanediyl group, preferably in which $W^{1+}$ is a group of formula:

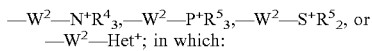

$W^2$ is alkanediyl of 1 or more, preferably 2-6 carbon atoms optionally containing one or more ethylenically unsaturated double or triple bonds, di substituted-aryl (arylene), alkylene arylene, arylene alkylene, or alkylene aryl alkylene, cycloalkanediyl, alkylene cycloalkyl, cycloalkylalkylene or alkylene cycloalkyl alkylene, which group $W^1$ optionally contains one or more fluorine substituents and/or one or more functional groups; and either the groups $R^4$ are the same or different and each is hydrogen or alkyl of 1 to 4 carbon atoms, preferably methyl, or aryl, such as phenyl, or two of the groups $R^4$ together with the nitrogen atom to which they are attached form an aliphatic heterocyclic ring containing from 5 to 7 atoms, or the three groups $R^4$ together with the nitrogen atom to which they are attached form a fused ring structure containing from 5 to 7 atoms in each ring, and optionally one or more of the groups $R^4$ is substituted by a hydrophilic functional group;

the groups $R^5$ are the same or different and each is $R^4$ or a group $OR^4$ where $R^4$ is as defined above; and Het is an aromatic nitrogen-, phosphorus- or sulphur-, preferably nitrogen-, containing, ring, for example pyridine.

Compounds in which Z is of the general formula in which $W^+$ is $W^1N^+R^4_3$ may be made as described in WO9301221. Phosphonium and sulphonium analogues are described in WO9520407 and WO9416749. Compounds in which Z is of this general formula in which $W^{1+}$ is $W^2N^+R^4_3$ are preferred.

Generally a Z-group of the formula 5 has the preferred general formula 6

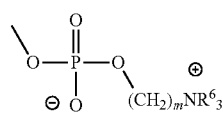

6 where the groups $R^6$ are the same or different and each is hydrogen or $C_{1-4}$ alkyl, and m is from 1 to 4, in which preferably the groups $R^6$ are the same preferably methyl. A particularly preferred example of this W group is the phosphorylcholine group:

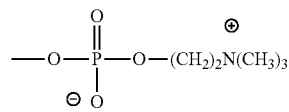

In phosphobetaine based groups, Z may have the general formula 7

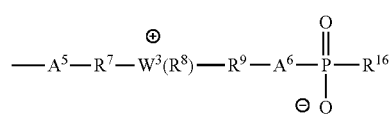

7 in which
$A^5$ is a valence bond, —O—, —S— or —NH—, preferably —O—;
$R^7$ is a valence bond (together with $A^5$) or alkanediyl, —C(O)alkylene-or —C(O)NH alkylene preferably alkanediyl, and preferably containing from 1 to 6 carbon atoms in the alkanediyl chain;
$W^3$ is S, $PR^8$ or $NR^8$;
the or each group $R^8$ is hydrogen or alkyl of 1 to 4 carbon atoms or the two groups $R^8$ together with the heteroatom to which they are attached form a heterocyclic ring of 5 to 7 atoms;
$R^9$ is alkanediyl of 1 to 20, preferably 1 to 10, more preferably 1 to 6 carbon atoms;
$A^6$ is a bond, NH, S or O, preferably O; and
$R^{10}$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Compounds comprising a group of the general formula 7 may be made by methods as described in JP03031718B, in which an amino substituted compound is reacted with a phospholane.

In compounds comprising a group of the general formula 7, it is preferred that
$A^5$ is a bond;
$R^7$ is a $C_{2-6}$ alkanediyl;
$W^3$ is $NR^8$, in which each $R^8$ is $C_{1-4}$ alkyl;
$R^9$ is $C_{2-6}$ alkanediyl;
$A^6$ is O; and
$R^{10}$ is $C_{1-4}$ alkoxy.

In phosphobetaines, such as those with groups of the formula 5 and 6, and non phosphobetaines such as those with groups of the formula 7, B is preferred to be a bond, a $C_{1\ to\ 6}$ branched or non branched alkanediyl group such as a methylene, ethylene propylene or butylene group, or a branched or non branched $C_{1-6}$ oxyalkylene group such as oxymethylene oxyethylene, oxypropylene or oxybutylene groups.

Where present, W is preferably independently selected from —OH, —COOH, —SO$_3$H, —O—(C$_2$H$_5$O)$_q$R$^1$, —O—(C$_{1-4}$alkyl)R$^2$, (C=O)—O— C$_{1-4}$ alkyl and —O— (C=O)C$_{1-4}$alkyl; and particularly —OH, —COOH, —SO$_3$H, —O—(C$_2$H$_5$O)$_q$R$^1$, —O—(C$_{1-4}$alkyl)R$^2$; wherein —SO$_3$H, —COOH and phenolic —OH, maybe in the form of a pharmaceutically acceptable salt;

In any of the polymers herein, where W is —O—(C$_{1-4}$ alkyl)R$^2$, it is preferably —O—(C$_{2-4}$alkyl)R$^2$ and more preferably —O—(C$_3$alkyl)R$^2$ or —O—(C$_4$alkyl)R$^2$.

The linker, X is preferably either a bond or is a linking group having 1 to 4 carbons and optionally 1 heteroatom selected from O and N; and is more preferably selected from a bond, $(C_{1-4})$alkylene, $(C_{1-4})$oxyalkylene, amino$(C_{1-4})$alkylene. Particular examples include a bond, $C_1$, $C_2$ or $C_3$ alkylene, oxymethyl or oxyethyl, aminomethylene and aminoethylene. Where a linker is present it is particularly a methylene, oxymethylene or amino methylene. Most preferably the ring is directly bonded to the group G, such that X is a bond.

q is preferably 1, 2 or 3; particularly 2 or 3;
n is preferably 2 or 3 and most preferably 3;
$R^1$ is preferably H or methyl; and
$R^2$ is preferably —COOH or —SO$_3$H.

In a preferred embodiment, the iodinated pendant groups of the formula 4a are groups where G is an ester linkage and X is a bond or a $(C_{1-4})$alkylene group. In a further preferred embodiment, groups of the formula 4a are groups where, G is an ether linkage and the linker, X, is a bond or a $(C_{1-4})$alkylene group, particularly a $(C_{1-4})$ alkylene group. In a further preferred embodiment, groups of the formula 4b are groups wherein the linker X is a bond, $(C_{1-4})$alkylene, $(C_{1-4})$oxyalkylene, amino$(C_{1-4})$alkylene. In this embodiment, particular preferred examples of X include a bond, $C_1$, $C_2$ or $C_3$ alkylene, oxymethyl or oxyethyl, aminomethylene and aminoethylene. In this embodiment, where a linker is present it is particularly a methylene, oxymethylene or amino methylene and most preferably, in this embodiment, X is a bond. In each of these preferred embodiments, the polymer preferably is or comprises PVA.

For the reasons given above, where the pendant group is formed after the polymer is cross linked, pendant groups of the formula IVa are preferred, particularly where G is selected from ether, ester, amide, carbonate, carbamate, and most particularly ether or ester.

Preferably the iodinated pendant groups comprises a phenyl ring substituted by 2, 3 or 4 iodines only, particularly 2 or 3 iodines only or is a phenyl group substituted in one or more of the following ways:

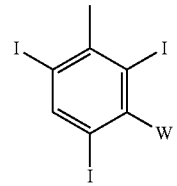

A

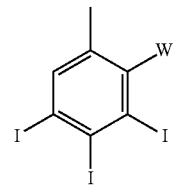

B

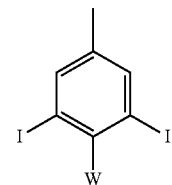

C

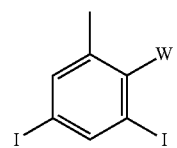

D

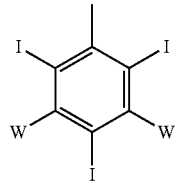

E

In particular the iodinated pendant groups comprises a phenyl ring substituted by 2, 3 or 4 iodines only, particularly 2 or 3 iodines only or a phenyl group substituted in one or more of the following ways:

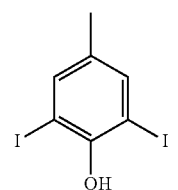

H

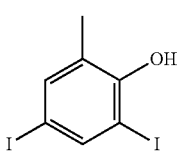

H

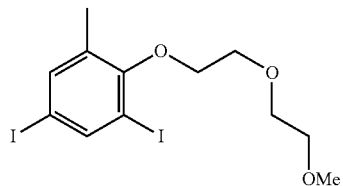

J

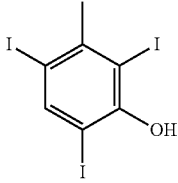

K

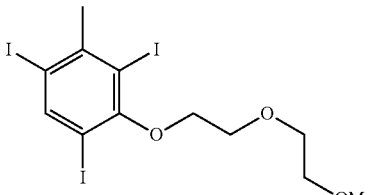

L

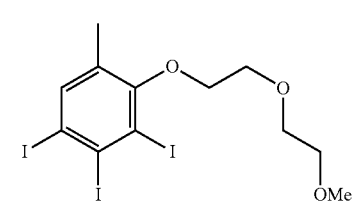

M

-continued

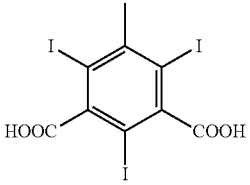

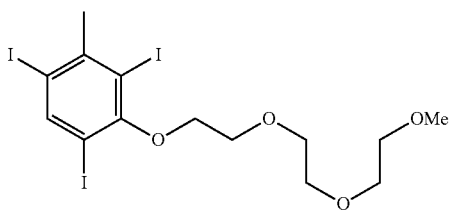

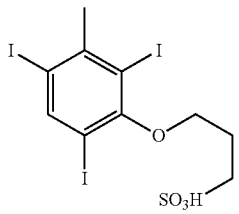

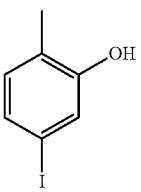

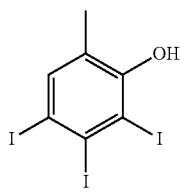

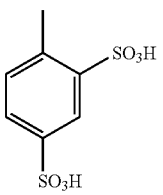

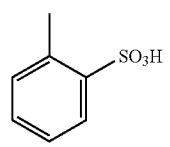

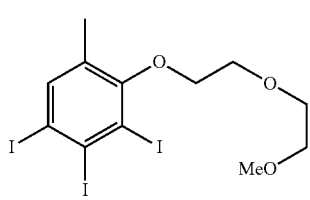

-continued

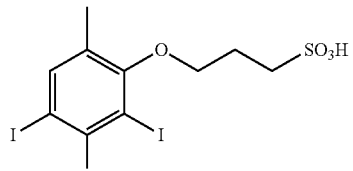

the iodinated phenyl group being

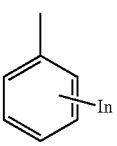

where n is 2 to 4, particularly 2 or 3; and particularly:

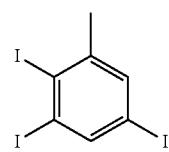

wherein —COOH, —SO₃H and phenolic —OH may be in the form of a pharmaceutically acceptable salt such a metal salt including sodium or potassium.

Methods of coupling iodinated phenyl aldehydes and iodinated phenyls with similar functional groups, to PVA are described in WO2015/033093.

Radiopaque biodegradable polymers where G is an ester linkage, may be prepared by reacting a polyhydroxylated polymer such as PVA with a compound of the formula 8

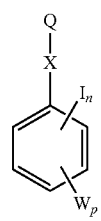

Where Q is a carboxylic acid, an acid halide (such as Cl or Br) or an activated carboxylic acid.

Where Q is a carboxylic acid the reaction is typically carried out under acid conditions (e.g. sulphuric acid, trifluoroacetic acid, trifluoromethane sulphuric acid, hydrobromic acid in acetic acid, acetic acid & methanesulfonic acid) in an appropriate polar solvent (e.g. DMSO, DMF, NMP).

Where Q is an acid halide the reaction is typically carried out under mild basic conditions in an appropriate polar solvent (e.g. DMSO, DMF, NMP) for example in the presence of a mild base (e.g. pyridine, trimethylamine, lutidine, collidine or imidazole).

Where Q is an activated carboxylic acid, activating agents such as carbodiimides and carbodiidazoles e.g. DCC (N,N'- dicyclohexylcarbodiimide), EDCI (N-(3-dimethylaminopropyl)-N'-ethylcarbodiimide) and HOBt (hydroxybenzotrazole) may be used in polar aprotic solvents, such as DMSO, tetrahydrofuran, ethyl acetate, acetone, dimethylformamide and acetonitrile. The reaction is typically carried out in the presence of a catalytic amount of a base and under anhydrous conditions to achieve activation. The base is typically of moderate strength (pKa of conjugate acid around 10-13) and suitable bases include a variety of pyridines, amines nitrogen heterocycles, triethylamines, N,N-diisopropylethylamine, DMAP and the like.

Coupling iodinated phenyl groups to PVA via an ester linkage, is discussed and exemplified in WO2011/110589 (e.g. preparation examples 1 to 6 therein), WO2014/152488 and Mawad et al (2009) Biomaterials, 30, 5667-5674, for example.

For the formation of ether linkages, a polyhydroxylated polymer, such as PVA may be reacted with a compound of the formula 8 wherein Q is a group selected from halides, such as fluoride, chloride, bromide, iodide; methylsulfonate, methyltoluenesulfonate, trifluoromethane-sulfonate. Q may be for example bromine.

Coupling iodinated phenyl groups to PVA via an ether linkage, is discussed in WO2011/110589 (see examples 1 and 2 therein).

Where the polymer is a polyhydroxylated polymer having 1,2 diol groups such as many polysaccharides or 1,3 diol groups, such as PVA, a radiopaque biodegradable polymer where G is a 1,3 dioxolane or a 1,3, dioxane may be prepared by reacting the polymer with a compound of the formula 8 wherein Q is a functional group such as aldehydes, acetals, and hemiacetals. Coupling iodinated groups to PVA in this manner, is described in WO2015/033092.

Polymers where G is a carbonate linkage may be prepared by reaction of the polyhydroxylated polymer with a compound of the formula IV where Q is a chloroformate group, such as formula 9.

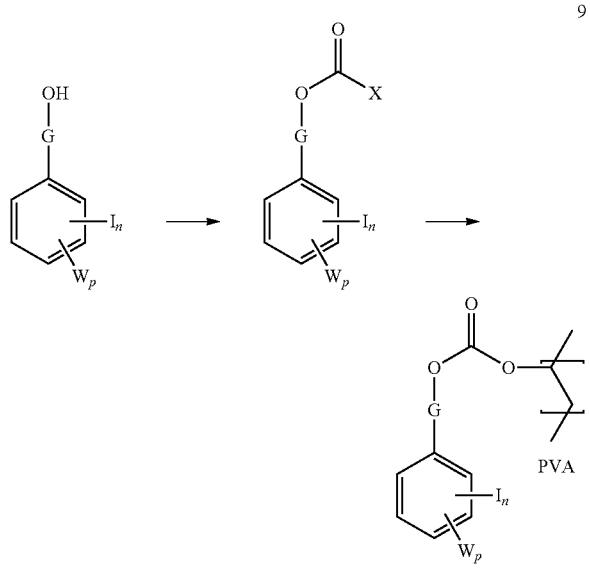

Whilst polymers where G is a carbamate linkage may be prepared by reaction of the a polyhydroxylated polymer with a compound of the formula 8 where Q is a carbamoyl chloride group, such as formula 10 or an isocyanate group such as formula 11:

Both of these reactions are mediated by a mild base, such as pyridine, trimethylamine lutidine, collidine or imidazole.

Radiopacity or radiodensity, may be varied as required by adjusting the amount of iodine in the polymer. This can be achieved by varying the number of iodines on the ring or by varying the proportion of pendant group to polymer.

Polymers of the invention preferably comprise at least 10 mg of iodine per cm$^3$, preferably 25 mg/cm$^3$, more preferably at least 50 mg/cm$^3$ and especially at least 100 mg/cm$^3$.

The quantity of iodine in the polymer may be at least 10%, preferably at least 20%, more preferably at least 30% and most preferably at least 35% wt/wt polymer by dry weight. High radiodensity in these polymers can be obtained where iodine is greater than 40% wt/wt dry polymer.

Preferably the polymer of the invention has a radiodenisty of at least 1000 HU or 2000 HU more preferably at least 3000 HU and particularly at least 4000 HU. When measured at 65 kV, especially as measured according to Example 13

The polymer backbone may also comprise other pendant groups such as one or more chelating species, such as mercaptoacetyltriglycine (MAG-3), EDTA EGTA, BAPTA, DOTA, DTPA-monoamide, DOTA-R, D03A-R, NOTA-BnR, NODASA-R, and NODAGA-R.

The chelating species my then be used to chelate a variety of metallic or non metallic species, which may include X-ray imageable elements, such as bismuth; alpha, beta or gamma emitting medical radioisotopes, such as Technetium-99 (Tc-99), cobalt-60, Iodine-131, Iridium-192, iodine-125, palladium-103, strontium-89, samarium-153, Rhenium-186, Lutetium-177, bismuth-213, lead-212, Yttrium-90, Iodine-131, Caesium-131, palladium-103, radium-223, actinium-225 and Holium-166, positron emission imageable elements such as Ga-68, Zr-89 or Rb-82 or, paramagnetic species such as, iron magnesium, molybdenum and tanatalum.

Examples of such chelating groups and methods for coupling them to polymers and particularly microspheres are disclosed in, for example, WO18093566A1, WO14159759A1 and WO08034911A1

Preferably the polymer is a hydrogel that is to say, the polymer is water-swellable but water-insoluble. In the presence of aqueous liquid, therefore, the polymer will form a hydrogel. It may comprise greater than 50% and preferably up to 98% water by weight, preferably 60 to 95 or 60 to 85%.

Alpha-ketoglutarate hydrogels made according to the invention may have water content of between 80% and 98% w/w. The water content may be altered when pendant groups are added.

A further aspect of the invention provides a microparticle comprising the cross-linked polyhydroxylated polymers described herein. In an embodiment of this aspect of the invention, the microparticles are suitable for use in the embolization of a blood vessel. Typically such microparticles are microspheres. The polymer microspheres typically have an average largest diameter of up to 2000, um, although the actual size ranges used will depend inter alia on the clinical need. Such particles may be prepared in any sub size range required, for example by sieving. Typical size ranges include 30-70, 70-150, 100-300, 300-500, 500-700 and 700-900 um, although smaller size ranges may be advantageous in some circumstances due inter alia, to their more distal embolisation properties. Such smaller size ranges include 70-150 or 40 to 90 um. Typically sizes less than 20 um are avoided due to off target embolisations caused by passage through the capillary bed; thus a lower practical limit is around 20-30 um. Sizes in the range 40 to 700 um, are currently most commonly used in clinical practice. The polymer used may be charged as described herein, so that the microspheres are suitable for loading drugs by ionic interaction.

In a particular embodiment, the polymer has a net charge at physiological pH, preferably a net negative charge at physiological pH (7.4).

The polymers of this embodiment may be used in composition with suitable a pharmaceutically acceptable carrier or diluent, such as water for injection, and may be used directly to embolise a blood vessel. Consequently pharmaceutical compositions comprising polymers described herein form a further aspect of the invention.

Alternatively, or additionally, an effective amount of one or more biologically active agents can be included in the compositions. It may be desirable to deliver the active agent from a polymer in the form of a hydrogel. Biologically active agents that it may be desirable to deliver include prophylactic, therapeutic, and diagnostic agents including organic and inorganic molecules and cells (collectively referred to herein as an "active agent", "therapeutic agent" or "drug"). A wide variety of active agents can be incorporated into the polymers. Release of the incorporated active agent from the polymer is achieved by diffusion of the agent from the polymer, degradation of the polymer, and/or degradation of a chemical link coupling the agent to the polymer. In this context, an "effective amount" refers to the amount of active agent required to obtain the desired effect.

The active agent is preferably reversibly held within the polymer. The agent may be reversibly bound within the polymer by ionic interaction, such as by interaction with positively or negatively charged groups of the polymer as described herein, alternatively, the agent may be held within the polymer by another means such as precipitation (see for example WO207/085615 or WO2007090897).

The active agent may be a chemotherapeutic agent, an antibody such as cetuximab, trastuzimab and nivolumab, an antibody fragment, a peptide, a low molecular weight protein, or a combination thereof.

Exemplary chemotherapeutic agents include the anthracycline class such as but not limited to doxorubicin, daunarubicin, epirubicin and idarubicin; the camptothecin class such as but not limited to irinotecan, topotecan, and exatecan; the platins such as cisplatin, oxaliplatin, carboplatin and miriplatin; mitomycin C, antimetablites such as 5-fluorouracil; multityrosine kinase inhibitors such as but not limited to sorafenib, sunitinib, regorafenib, brivinb, dasetanib, bosutinib, erlotinib, gefitinib, imatinib and vandetinib, rapamycin or any combination thereof. Where such compounds are ionisable, such compounds may be typically used in their ionic forms.

A further aspect of the present invention provides methods of medical treatment comprising delivering a polymer as described herein, to a blood vessel of a subject in need thereof, such as to form an embolus. The polymer may be in the form of a microsphere or other particulate form. The polymer may comprise a an effective amount of one or more biologically active agent. The polymer may be delivered in combination with an X-ray contrast agent, for example the polymer, in the form of microspheres may be suspended in the contrast agent before delivery, or the agent may be delivered immediately before or after the polymer. The polymer may be delivered by the transcatheter route, particularly when in the form of microspheres.

The treatment may be a treatment of a hypervascular tumour, for example by trans arterial embolisation or chemoembolization, but the polymer may also be delivered by local injection, for example of microspheres, which may for example provide a depot of drug.

In a further aspect, the polymer may be used in the preparation of implantable medical devices such as sutures, stents, fiducial markers or tissue separators (for use, for example, by positioning between two tissues during a procedure to separate one from the other), or as a coating for medical devices.

In a still further aspect the invention provides a method of making a biodegradable polymer microsphere comprising:
providing a first liquid, which is a solvent having dissolved therein (i) a polymer which is or comprises PVA and (ii) a compound of the formula 2 wherein Q and X are as described herein:

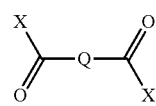

2 providing a second liquid which is immiscible with the first liquid;
bringing the first liquid into contact with the second liquid such that the first liquid forms a discontinuous phase within the second liquid; and crosslinking the PVA with the compound of the formula 2 within the discontinuous phase such as to form a microsphere.

Bringing the first liquid into contact with the second liquid preferably forms an emulsion, wherein the droplets of the first phase within the second are of a of a size suitable to provide microspheres of the required size. The emulsion will typically be maintained by vigorous mixing.

The solvent may be a polar aprotic solvent as described above. The second liquid may be an oil, such as mineral oil. The reaction may proceed in the presence of an emulsifying agent, such as a surfactant (eg SPAN 20).

Following the formation of polymer microspheres, which may proceed over a period of 1 hr to 24 hrs, the microspheres may be recovered.

The invention will now be described further by way of the following non limiting examples with reference to the figures. These are provided for the purpose of illustration only and other examples falling within the scope of the claims will occur to those skilled in the art in the light of these. All references cited herein are incorporated by reference in their entirety. Any conflict between that reference and this application shall be governed by this application.

FIGURES

Figure 4:
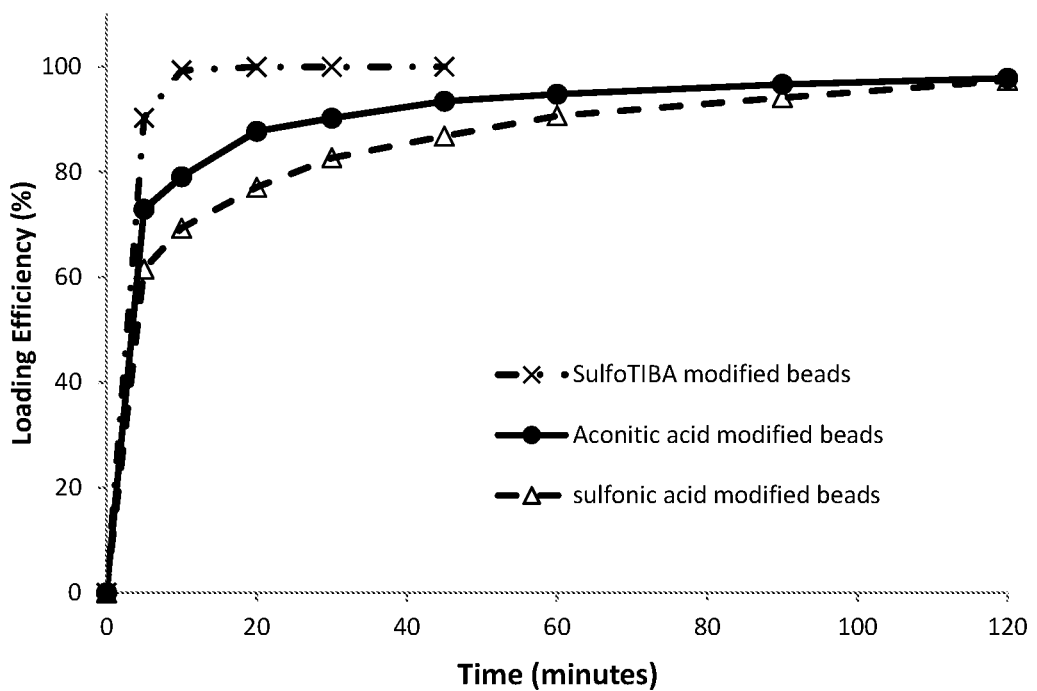

FIG. 4. illustrates drug loading curves for doxorubicin loading of 4 microsphere preparations.

EXAMPLES

Example 1. Synthesis of PVA-Alpha-Ketoglutarate Degradable Polymers as Microspheres PVA (10 kDa Mw, 1.0 g, 0.1 mmol, 1 eq) was dissolved in 1-methyl-2-pyrrolidinone (4 ml) with gentle heating to 90° C. under inert atmosphere, then allowed to cool to room temperature. Alpha-ketoglutaric acid (KGA 0.06 g, 0.42 mmol, 4.2 eq) and 1,1'-carbonyldiimidazole (CDI, 0.15 g, 0.91 mmol, 9.1 eq) were dissolved in 1-methyl-2-pyrrolidinone (2 ml), respectively, followed by mixing the two solution to form an imidazole intermediate over 5 minutes at ambient temperature.

To a dried 1L round bottom flask, heavy or light mineral oil (500 ml) and surfactant Span20 (6 ml) were mixed with a mechanical stirring under a nitrogen blanket, and the reaction flask was heated to temperature 70° C. The PVA 1-methyl-2-pyrrolidinone solution was mixed with the CDI-activated alpha-ketoglutaric acid solution. The mixture was roller-mixed for about 20 to 30 minutes at ambient temperature. Then the brown coloured solution was added in to the mineral oil solution under a nitrogen blanket and with strong stirring. The suspended micro droplets gradually solidified into microparticles over the course of 1 to 10 hours at 70° C.

When the reaction stopped, the suspension was allowed to settle, and the mineral oil was aspirated and the resulting micro particles were washed with alkyl acetate (2×500 ml) and ethanol (2×500 ml) in sequence. The washed particles were transferred into saline solution at pH 3 and the swollen microparticles were sieved for the collection of fractions of different size range, 32-70 μm, 70-150 μm, 150-300 μm, 300-500 μm and 500 to 700 μm. The collected microparticles were placed into acetone to remove water, followed by vacuum drying at ambient temperature for 24 hour. Element analysis results showed that the nitrogen level of the dry microparticles was not detectable from the background, which is indicative of a clean wash of imidazole, a by-product. The microparticles were gamma-sterilized using a dose of 25 kGy.

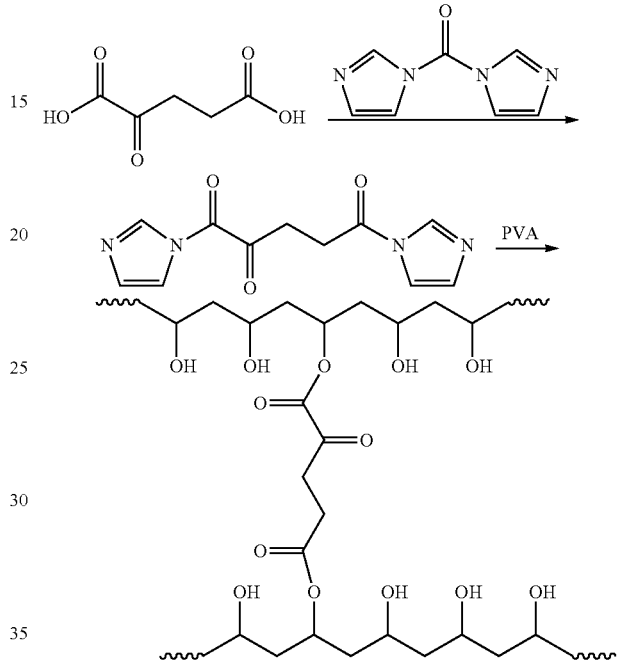

Example 2. Synthesis of Biodegradable PVA-Fumaric Acid Polymers

PVA (10 kDa Mw, 1.0 g, 0.1 mmol, 1 eq) was dissolved in 1-methyl-2-pyrrolidinone (4 ml) with gentle heating under inert atmosphere. Fumaric acid (0.08 g, 0.7 mmol) and 1,1'-carbonyldiimidazole (CDI, 0.22 g, 1.4 mmol) were dissolved in DMSO (2 ml), respectively, followed by mixing the two solutions to form an imidazole intermediate over 10 minutes at ambient temperature.

To a dried 1L round bottom flask, heavy or light mineral oil (500 ml) and surfactant Span20 (6 ml) were mixed with a mechanical stirring under a nitrogen blanket, and the reaction flask was heated to temperature 70° C. The PVA 1-methyl-2-pyrrolidinone solution was mixed with the CDI-activated fumaric acid solution. The mixture was roller-mixed for about 20 to 30 minutes at ambient temperature. Then the brown coloured solution was added in to the mineral oil solution under a nitrogen blanket and with strong stirring. The suspended micro droplets gradually solidified into microparticles over the course of 15 hours at 70° C.

The work up of the fumaric acid cross-linked beads was the same as in Example 1.

Example 3. Synthesis of PVA-Succinic Acid Biodegradable Polymers

PVA (10 kDa Mw, 1.0 g, 0.1 mmol, 1 eq) was dissolved in 1-methyl-2-pyrrolidinone (5 ml) with gentle heating under inert atmosphere. Succinic acid (0.08 g, 0.7 mmol) and 1,1'-carbonyldiimidazole (CDI, 0.24 g, 1.5 mmol) were dissolved in 1-methyl-2-pyrrolidinone (2 ml), respectively, followed by mixing the two solutions to form an imidazole intermediate over 5 minutes at ambient temperature.

To a dried 1 L round bottom flask, heavy or light mineral oil (500 mL) and surfactant Span20 (6 mL) were mixed with a mechanical stirring under a nitrogen blanket, and the reaction flask was heated to temperature 70° C. The PVA 1-methyl-2-pyrrolidinone solution was mixed with the CDI-activated succinic acid solution. The mixture was roller-mixed for about 20 to 30 minutes at ambient temperature. Then the mixture was added into the mineral oil solution under a nitrogen blanket with strong stirring at about 300 rpm. The suspended micro droplets gradually solidified into microparticles over the course of 2 to 10 hours at 70° C. The work up of the fumaric acid cross-linked beads was the same as in Example 1.

Example 4. Synthesis of Biodegradable PVA-KGA Polymers with High PVA Solid Content Following the example 1, PVA (Mw 10 kDa, 1.50 g, 0.15 mmol, 1 eq) α-Ketoglutaric acid (0.15 g), 1,1'-Carbonyl-diimidazole (0.38 g), were used to synthesis microparticles in heavy mineral oil 500 mL. Span 20 was used to stabilise the suspended droplets. The reaction was carried out at 70° C. for 15 hours, and the micrparticles generated were processed as per example 1.

Example 5. Synthesis Biodegradable PVA-KGA Polymers with 3 kDa PVA

Following the procedure in Example 1, PVA (3 kDa Mw, 1.00 g, 0.10 mmol, 1 eq) α-Ketoglutaric acid (0.10 g, 0.7 mmol, 7 eq), 1,1'-Carbonyldiimidazole (0.25 g, 1.5 mmol, 15.5 eq), were used to synthesize biodegradable micropar-ticles in heavy mineral oil. Span 20 was used to stabilise the suspended droplets. The reaction was carried out at 70° C. for 2 to 15 hours, and the microparticles generated were processed as the example 1.

Example 6. Polymer Degradation Study

Figure 1:
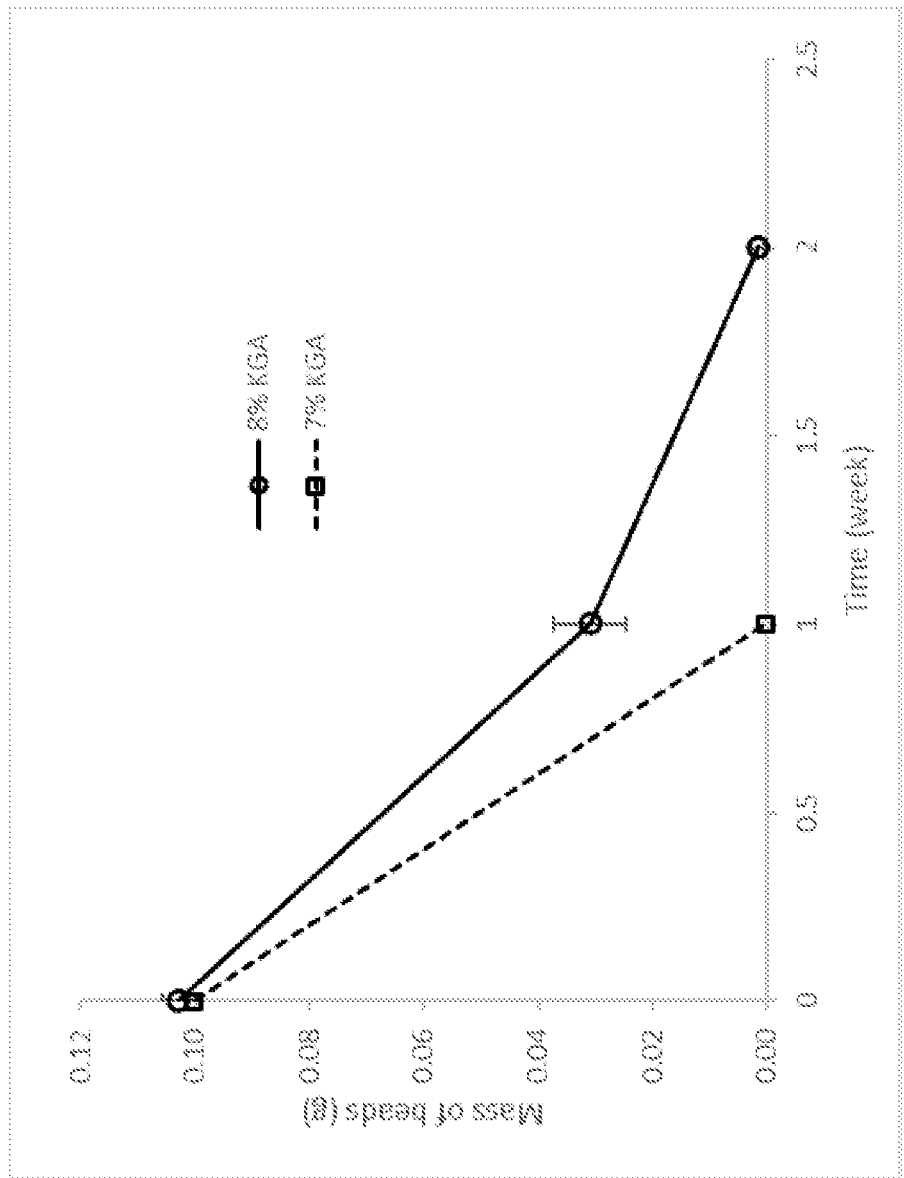
FIG. 1 shows degradation of biodegradable polymers measured according to example 6.
Figure 2:
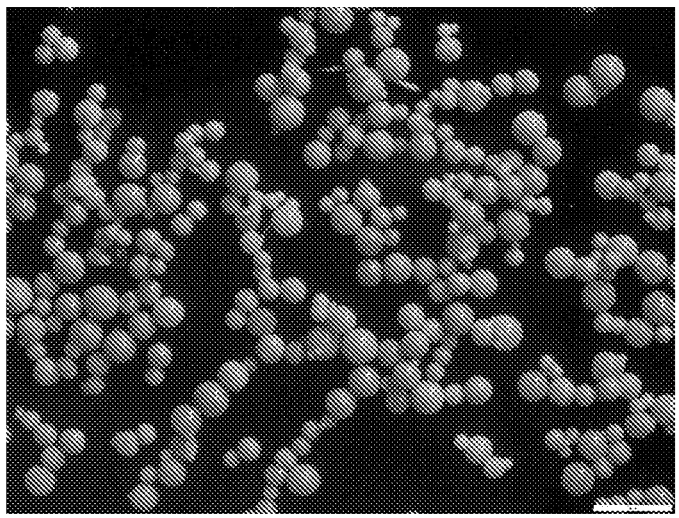
FIG. 2 shows an image of biodegradable polymers (125-300 μm) in dry state (A) hydrated in saline (B) and after catheter delivery (C)
Figure 2:
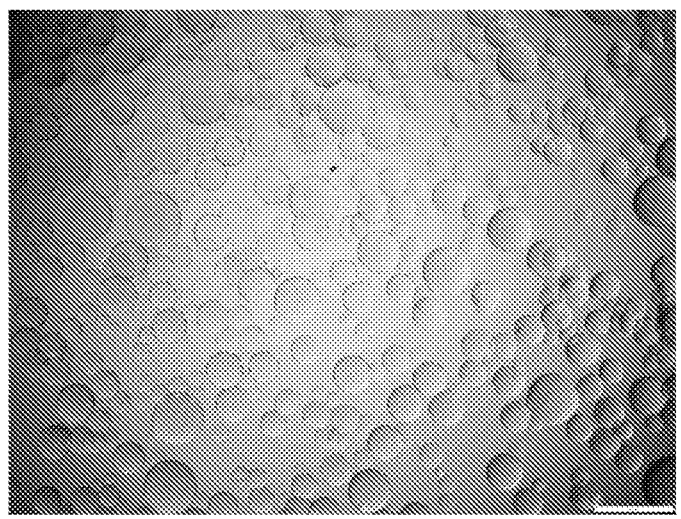
Figure 2:
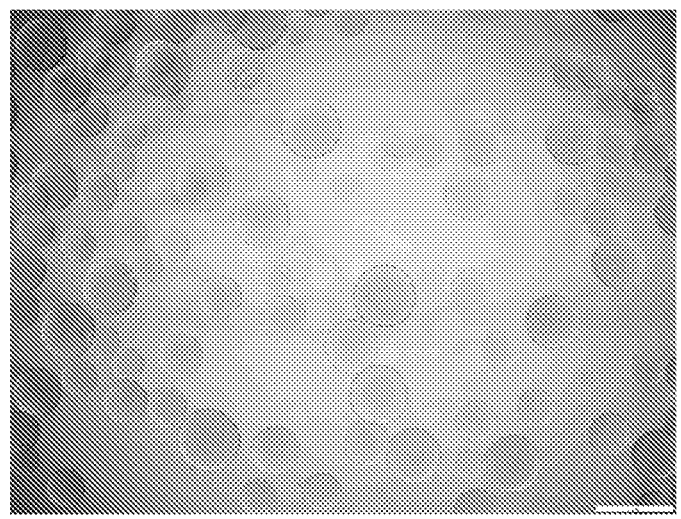

Three groups of 0.1 g of dry microparticles of size range 60 to 300 um were pre-weighed and placed into 100 mL of Phosphate Buffered Saline (PBS: NaCl 136.7 mM, KCl2.7 mM, Na2HPO4 10.1 mM, KH2PO4 1.7 mM) in a Duran® bottle (pH 7.4, in each group n=3). The microparticles in PBS were incubated at 37° C. with occasional agitation. Microparticles were periodically collected by filtration using a 40 um sieve, vacuum dried and weighed. The filtered solution was analysed by Gel Permeation Chromatography directly. A sample of raw material of PVA polymer used for microparticle synthesis was also analysed a as control. The Gel Permeation Chromatography of the samples were com-pared to PEG standards and PVA reference to determine the molecular weight and distribution of the degradation prod-uct. The weight change of the microparticles during degra-dation are shown in FIG. 1.

Example 7. Solid Content, Suspension and Catheter Delivery Test

The solid content of biodegradable microparticles (PVA-KGA 8%) were tested with four size ranges 32 to 70 μm, 70 to 125 μm, 125 to 300 μm and 300 to 500 μm. The test was carried out by accurately weighing the dry microparticles, followed by saline hydration of the microparticles to satu-ration. To obtain the weights of hydrated microparticles, extra saline was removed by pipetting and tissue wicking. The solid content of the microparticles are listed in the Table 1.

TABLE 1

| Solid content of hydrated microparticles | |
|---|---|
| Microparticle size range | Solid content (% w/w) |
| 32-70 μm | 7.4 ± 0.7 |
| 70-125 μm | 11.8 ± 0.2 |
| 125-300 μm | 12.5 ± 1.2 |
| 300-500 μm | 11.8 ± 0.8 |

Table 2 illustrates the effect of various KGA levels on the solid content of microspheres prepared according to the above examples

TABLE 2

| Solid content (% w/w) of hydrated microparticles with varying KGA content. | | | |
|---|---|---|---|
| KGA level in beads | 75-125 μm | 125-300 μm | 500-700 μm |
| 6.5% | 6.06 ± 0.94 | 6.61 ± 0.23 | 7.88 ± 0.61 |
| 8.0% | 7.95 ± 1.26 | 7.81 ± 0.17 | 11.11 ± 0.31 |
| 10.0% | 8.09 ± 0.79 | 10.14 ± 0.38 | 12.73 ± 0.21 |

For the suspension test, 50 mg dry microparticles were hydrated in 5 mL of saline and mixed with contrast medium, Omnipaque 350, to achieve stable suspensions over the course of 5 minutes. An optimal ratio of Omnipaque 350: saline was found around 4-5:5 (v/v, mL). Catheter delivery of the microparticles was carried out by injecting the microparticles suspension through a 2.4 Fr Progreat catheter. All four size ranges were delivered through the catheter without blockage. The ease of delivery of the microparticles increased with decreasing microparticle size, i.e. the 32 to 70 μm size range were the easiest to deliver, followed by 70 to 125 μm microparticles, 125 to 300 μm microparticles and 300 to 500 μm microparticles. After delivery, microscope images showed no evidence of microparticle damage.

Example 8. General Protocol for Coupling Iodinated Phenyl Aldehydes and Aldehyde Derivatives to PVA To a pre-dried reactor under a nitrogen blanket is added PVA (typically 5-10 g) and anhydrous solvent (typically DMSO or NMP, 40 vol w.r.t. PVA mass) and catalyst (typically 2.2 vol w.r.t. PVA mass. eg methanesulphonic acid). The stirred suspension is heated to elevated tempera-ture (ca 90° C.) to dissolve the PVA. When a homogeneous solution had been obtained, the mixture is cooled to the desired reaction temperature (typically 50-80° C.) the desired aldehyde substrate for the first and second pendant groups (typically 0.01 to 0.6 eq PVA diol functionalities) are added. The actual ratio of first and second pendant group aldehyde substrate to PVA 1,3-diol groups, and the ratio of first to second pendant groups, will depend on the tuning of hydrophilic to hydrophobic nature of the polymer required, but typically the first pendant group will be at a higher ratio than the second.

The reaction is then stirred under an $N_2$ blanket and the reaction conversion is monitored by HPLC for consumption of substrate. At a pre-determined time (typically when consumption of the substrate has ceased) an anti-solvent is added (typically, acetone, DCM, MeCN or TBME, ca 40 vol) dropwise from a dropping funnel. The supernatant fluid is removed by aspiration through a filter membrane and further reaction solvent (typically 40 vol) is charged and stirred until the solids had fully dissolved. This solvent washing stage is repeated up to 3 times. Then the solid is re-dissolved in reaction solvent, and precipitated by the slow addition of water (typically up to 100 vol). The resulting aggregated solid is removed from the supernatant and homogenised in a blender in water. The suspension is filtered and re-suspended in water (typically 100 vol), slurried for up to 30 minutes and filtered. The water slurrying is repeated until pH neutral had been obtained, then the damp solids are slurried in acetone (100 vol, 30 mins stir, 2 repetitions), filtered and dried in a high vacuum oven at 30° C. for up to 24 hours.

Example 9. Coupling of 5-((2,2-Dimethoxyethyl) Amino)-2,4,6-Triiodo-Isophthalic Acid To a flame dried 500 ml rbf under nitrogen, was added solid 5-amino-2,4,6-triiodoisophthalic acid (46.95 g, 84.03 mmol, 1.0 eq), sodium bicarbonate (28.21 g, 335.8 mmol, 4.0 eq) and DMF (ca 400 ml) via cannula. To the resulting brown solution was added 2-bromo-1,1-dimethoxyethane (13 ml, 110.0 mmol, 1.3 eq) dropwise and the resulting solution heated to reflux for 18 h. After cooling to room temperature, the majority of DMF was removed by rotary evaporation under vacuum (9 mBar, 55° C.) and the resulting orange solid extracted with ethyl acetate (1L). This suspension was washed with saturated lithium chloride solution (7×400 ml) to remove residual DMF and salts, dried over magnesium sulfate, filtered and evaporated to dryness. The resulting solid was recrystallised from ethyl acetate, washed with i-hexane and filtered. This process was repeated a total of 3 times and the resulting orange solid dried under high vacuum to give the title compound (33.04 g, 61%, 91.7% HPLC purity). The product could be further purified via silica gel column chromatography (MeOH in DCM, 0-15%) (4.91 g, 82% yield, 96% HPLC purity); $\delta_H$ (CDCl$_3$, 500.1 MHz)/ppm; 8.01 (1H, s), 4.86 (2H, br s), 4.76 (1H, t, 5.5 Hz), 4.37 (2H, d, 5.5 Hz), 3.44 (6H, s); $\delta_C$ NMR (CDCl$_3$, 125.8 MHz)/ppm;

Dried microparticles prepared according to example 1(0.50 g) of various sizes, were added into a stirred solution of N,N-dimethylformamide (40 mL) to allow the microparticles to swell. Catalyst methane sulfonic acid (2.2 mL) and 5-((2,2-dimethoxyethyl)amino)-2,4,6-triiodoisophthalic acid (7.46 g, 11.5 mmol) were added into the reaction vessel. The temperature was raised to 70° C. under an inert atmosphere for 24 hours. After cooling to room temperature (approximately 15° C. to 25° C.), the microparticles were aspirated and then washed with dimethyl formamide (3×40 ml), ethanol (2×50 ml) and acetone (3×50 ml), respectively. After removing acetone, the microparticles were dried under vacuum at ambient temperature for 18 hours.

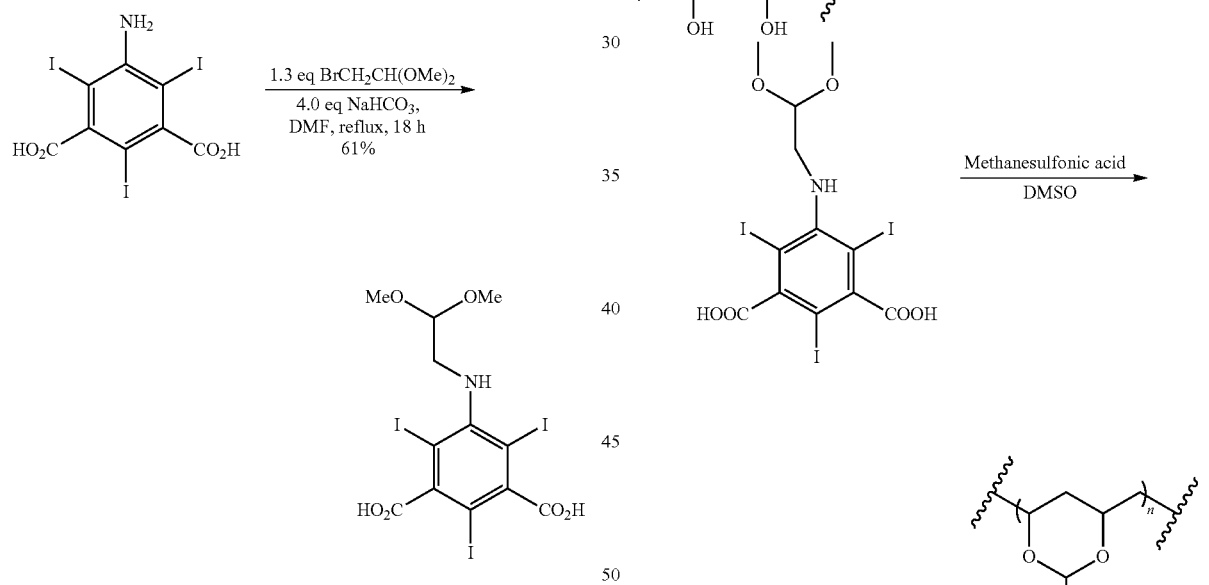

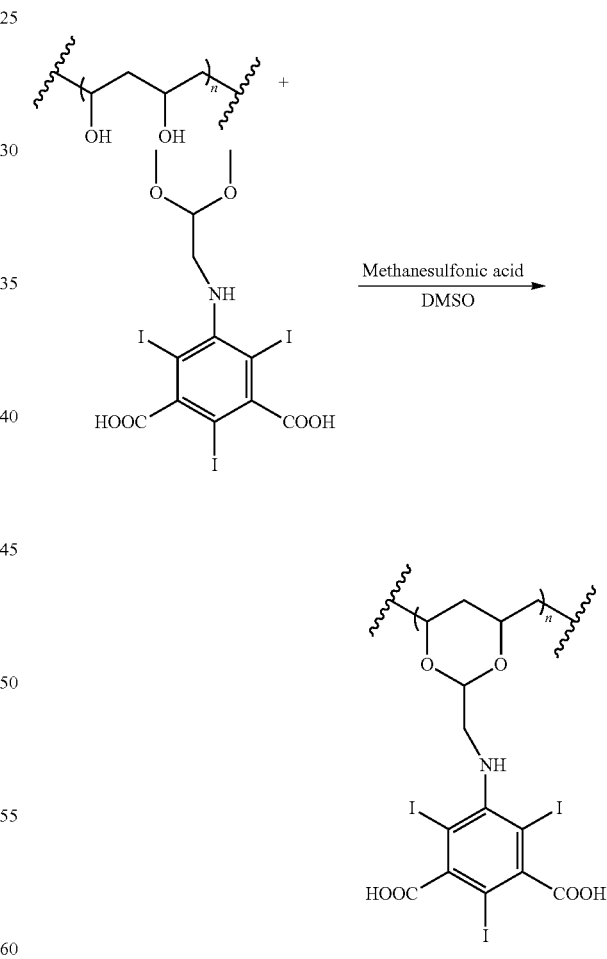

The radiodensity of these microspheres was determined according to example 13 to be 6288±450 HU. The microspheres were suspended in contrast medium and saline mixture (2:0.5-2:1, v/v) in about 1 minute. The beads were successfully delivered through 2.4 Fr Progreat catheter.

Figure 3:
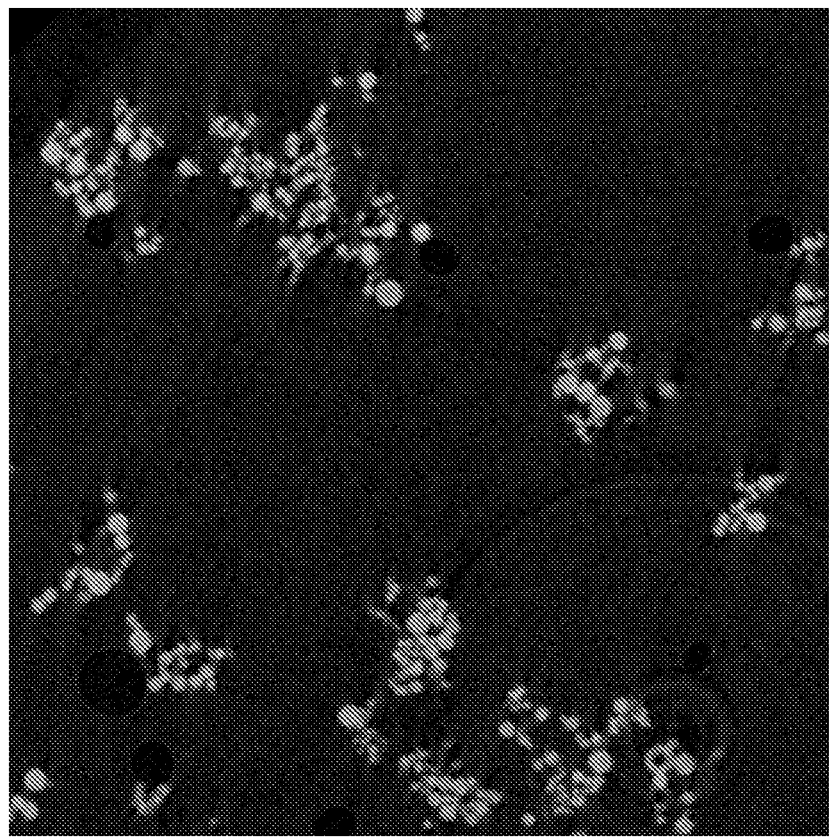
FIG. 3 shows a microCT image of microspheres prepared according to example 8

FIG. 3 shows a microCT image of these microsphere.

Example 10. Synthesis of Polymers with Sulfonated and Iodinated Phenyl Group: Synthesis of 3-(3-Formyl-2,4,6-Triiodophenoxy)Propane-1-Sulfonate and 3-(1-Formyl-3,4,5-Triiodophenoxy) Propane-1-Sulfonate, Sodium Salt

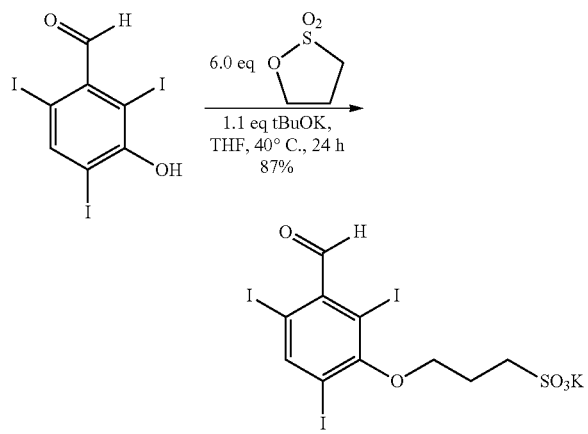

In a 150 mL three-neck round bottom flask, 3-hydroxy-2,4,6-triiodobenzaldehyde (10 g, 20 mmol) was dissolved in 50 mL anhydrous Tetrahydrofuran (THF) by magnetic stirrer. 2.47 g (22 mmol) of potassium t-butoxide was mixed with 20 mL of THF and the suspension was added slowly into the flask under nitrogen atmosphere at room temperature, followed by increasing temperature to 40° C. to allow a fully dissolution of product. Then 15 g (120 mmol) of sultone was dissolved in 15 mL of THF and the mixture was added slowly to the reaction flask. A precipitation appeared almost immediately. After 3 hr reaction at 40° C., the reaction mixture were poured into 500 mL of ethyl acetate to receive solid raw product. The filtered solid was washed with 100 mL of ethyl acetate, and recrystallized in ethanol. After vacuum drying over 24 hr, 10.7 g product was received with 80% yield. SulfoTIBA proton Nuclear Magnetic Resonance (NMR) analysis, D$_2$O solvent: δ (ppm) 2.24-2.34 (m, 2H), 3.12-3.25 (t, 2H), 3.88-4.02 (t, 2H), 8.18-8.25 (s, 1H), 9.42-9.50 (s, 1H). Element analysis result: C18.56, H 2.22, S 5.66, I 52.31, K 6.27. Cal: C 18.20, H 1.22, S 4.85, I 57.68, K 5.92.

3-(1-formyl-3,4,5-triiodophenoxy)propane-1-sulfonate, sodium salt was synthesized analogously from 3,4,5-triiodosalicylaldehyde (see example 19).

PVA Modification with Sodium 3-(3-Formyl-2,4,6-Triiodophenoxy)Propane-1-sulfonate (STIBA)

6.56 g of STIBA and 3.98 g of PVA (Mw 10 kDa) were dissolved into 40 mL of Dimethyl sulfoxide (DMSO) in a reaction flask. Catalyst methyl sulfonic acid 8.8 mL was mixed with 20 mL of DMSO and added into the flask. After 24 hours reaction at 60° C., the reaction mixture was precipitated twice in 900 mL of acetone with stirring. The collected solid was dissolved in deionised water and placed in a dialysis bag (MWCO: 1000). The polymer was dialysed against water for three days to remove small molecular impurities, followed by freeze-drying with 1.55 gram of polymer received.

3-(1-formyl-3,4,5-triiodophenoxy)propane-1-sulfonate prepared as above, may be coupled to PVA in an analogous manner. 2-sulfobenzaldehyde sodium salt, (Sigma Aldrich UK), 4-formylbenzene 1,3 disulfonic acid disodium-salt, (Sigma Aldrich UK), and 4-formylbenzoic acid (Sigma Aldrich UK) may also be coupled to PVA by using an analogous synthetic route.

Bead synthesis by using KGA cross-linker followed the same procedure in Example 1.

The STIBA-modified PVA obtained above was dissolved into 1-methyl-2-pyrrolidinone (5 mL). Alpha-ketoglutaric acid (0.06 g, 0.42 mmol) and 1,1'-carbonyldiimidazole (CDI, 0.15 g, 0.91 mmol) are dissolved in 2 mL 1-methyl-2-pyrrolidinone (2 mL), respectively, followed by mixing the two solution to form an imidazole intermediate over 5 minutes at ambient temperature. The PVA solution was then mixed with the CDI-activated alpha-ketoglutaric acid solution, followed by mixing with 500 mL of mineral oil and surfactant Span20 at 70° C. under mechanical stirring at 300 rpm. The suspended microdroplets gradually solidified into micro particles overnight. The received beads were then washed with ethyl acetate and ethanol to remove residual oil and reactants. The beads were vacuum dried.

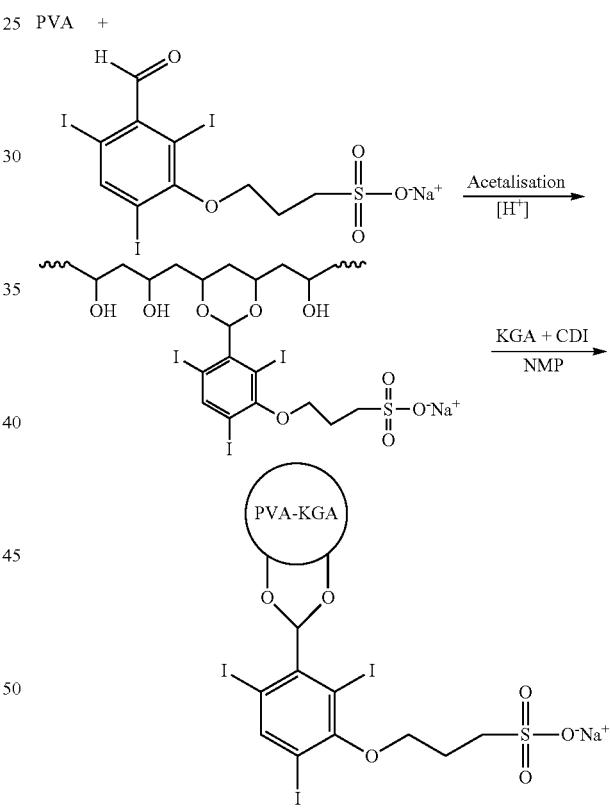

Example 11. Biodegradable Polymers with Pendant Carboxyl Groups 0.5 g of PVA microparticles prepared according to example 1 were dispersed into 35 mL of Dimethylformamide (DMF), followed by addition of cis-aconitic anhydride (0.442 g, 2.8 mmol) and triethylamine (0.525 ml, 3.8 mmol.). Reaction temperature was kept at 60° C. and stirred at 350 rpm for 24 h. After the reaction stopped, the microparticles were washed with 30 mL of DMF and PBS, followed by acetone washing. The microparticles were then vacuum dried overnight at room temperature (approximately 15° C. to 25° C.).

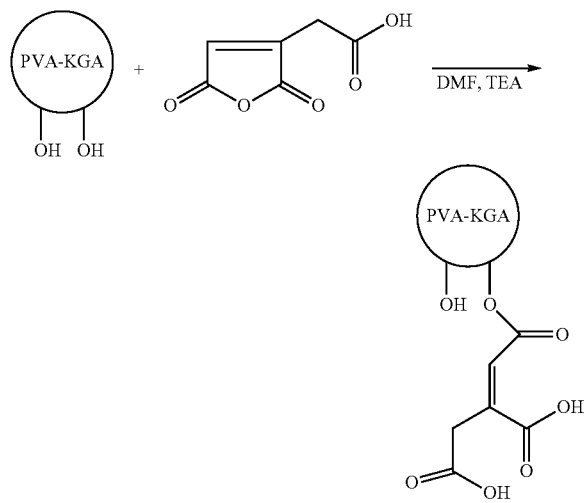

Example 12. Biodegradable Polymers with Pendant Sulphonyl Groups 0.5 g of PVA microparticles were dispersed into 35 mL DMF, followed by adding chlorosulfoacetyl chloride (1.00 g, 5.6 mmol) and Triethylamine (1.65 ml, 11.8 mmol). Reaction temperature was kept at 60° C. and the reaction mixture was stirred at 350 rpm for 24 hours. After the reaction stopped, the microparticles were washed with 30 mL of DMF and PBS to remove residual reactant. The microparticles were further processed by washing with acetone and following that vacuum drying.

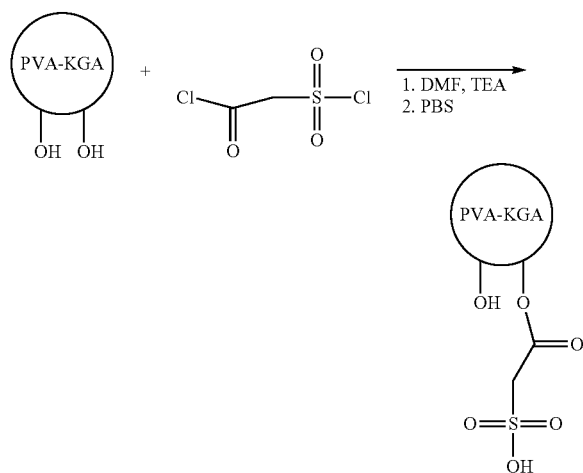

Example 13. Microspheres with Pendant Propionic Acid Groups

Crosslinked PVA microparticles are dispersed into 35 mL DMF, 3,3-dimethoxy propionic acid and methanesulfonic acid is added to react with the diol groups on the polymers. The microparticles are aspirated and then washed with dimethyl formamide, ethanol and acetone, respectively. After removing the acetone, the microparticles are dried under vacuum at ambient temperature.

Example 14. Radiodensity Determinations

Micro-CT was used to evaluate the radiopacity (radiodensity) of samples of radiopaque embolic beads prepared according to general example 8 above. The samples were prepared in Nunc cryotube vials (Sigma-Aldrich product code V7634, 48 mm×12.5 mm). The beads were suspended in 1% agarose gel (prepared with Sigma-Aldrich product code A9539). The resulting suspension is generally referred to as a "Bead Phantom". To prepare these bead phantoms, a solution of agarose (1%) is first raised to a temperature of approximately 50° C. A known amount of the beads is then added, and the two gently mixed together until the solution starts to solidify or gel. As the solution cools it gels and the beads remain evenly dispersed and suspended within the agarose gel.

Bead phantoms were tested for radiopacity using micro-Computer Tomography (Micro-CT) using a Bruker Skyscan 1172 Micro-CT scanner at the RSSL Laboratories, Reading, Berkshire, UK, fitted with a tungsten anode. Each phantom was analysed using the same instrument configuration with a tungsten anode operating at a voltage of 64 kV and a current of 155 μA. An aluminium filter (500 μm) was used.

TABLE 1

| Acquisition parameters: | |
|---|---|
| Software: | SkyScan1172 Version 1.5 (build 14) NRecon version 1.6.9.6 |
| CT Analyser version | 1.13.1.1 |
| Source Type: | 10 Mp Hamamatsu 100/250 |
| Camera Resolution (pixel): | 4000 × 2096 |
| Camera Binning. | 1 × 1 |
| Source Voltage | 65 kV |
| Source Current uA | 153 |
| Image Pixel Size (um): | 3.96 |
| Filter | Al 0.5 mm |
| Rotation Step (deg) | 0.280 |
| Output Format | 8 bit BMP |
| Dynamic Range | 0.000-0.140 |
| Smoothing | 0 |
| Beam Hardening | 0 |
| Post Alignment | corrected |
| Ring Artefacts | 16 |

A small amount of purified MilliQ® water was carefully decanted into each sample tube. Each sample was then analysed by X-Ray micro-computer tomography using a single scan, to include the water reference and the beads. The samples were then reconstructed using NRecon and calibrated against a volume of interest (VOI) of the purified water reference. A region of interest (ROI) of air and water was analysed after calibration to verify the Hounsfield calibration.

Radiodensity was reported in Hounsfield units from line scan projections across the bead. Values used for dynamic range for all samples in NRecon (thresholding): −0.005, 0.13 (minimum and maximum attenuation coefficient). The microspheres from example 5 measured according to this general protocol had a radiodensity of 6288±450 HU. The beads were suspended in contrast medium and saline mixture (2:0.5-2:1, v/v) in about 1 minute. The beads were successfully delivered through 2.4 Fr Progreat catheter.

Example 15: Synthesis of 3,5-Diiodo-2-(2-(2-Methoxyethoxy) Ethoxy) Benzaldehyde

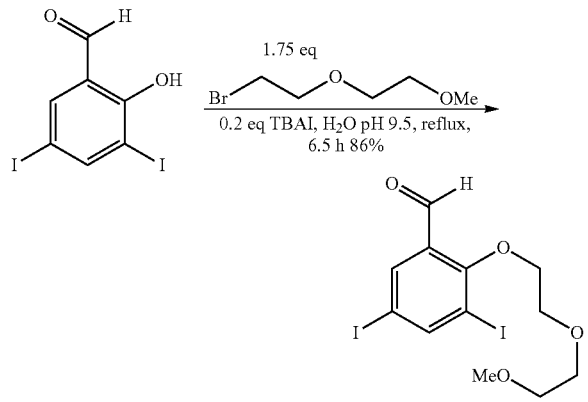

To a HEL PolyBlock8 parallel synthesis 125 ml reactor fitted with a reflux condenser and suspended magnetic stirrer, was added 3,5-diiodosalicylaldehyde (13.9011 g, 37.72 mmol, 1.0 eq) and TBAI (2.7481 mg, 0.802 mmol, 0.2 eq). To this was added water and the pH adjusted to 9.5 with 1M NaOH (total aqueous volume 97 ml). The reactor was set to 500 rpm stirring until full dissolution to give a bright yellow solution and 1-bromo-2-(2-methoxyethoxy)ethane (5.00 ml, 37.17 mmol, 1.0 eq) was added. The reactor zone was set to heat to 120° C. The reaction was monitored by TLC (30% EA in i-hex) and after 2 h additional bromide was added (2.50 ml, 18.59 mmol, 0.5 eq). After a further 0.5 h, the pH was readjusted to 9.5 due to consumption of the bromide. After a further 2 h additional bromide (1.25 ml, 9.29 mmol, 0.25 eq) were added and the reactor turned down to 50° C. and left to stir overnight. After 19h, the resulting suspension was reheated to reflux for 1 h, cooled to RT and transferred to a separating funnel in ethyl acetate (400 ml). The organics were washed twice with sat. sodium bicarbonate, dried with magnesium sulfate, hot filtered from toluene, and recrystallised from toluene/isohexane to give, after filtration and hi-vacuum drying, the desired product as a yellow powder (15.2909 g, 86.4% yield); $\delta_H$ (CDCl$_3$, 500.1 MHz)/ppm; 10.31 (1H, s), 8.31 (1H, d, 2.2 Hz), 8.09 (1H, d, 2.2 Hz), 4.26 (2H, app. t, 4.5 Hz), 3.89 (2H, app. t, 4.5 Hz), 3.67 (2H, app. t, 4.6 Hz), 3.55 (2H, app. t, 4.6 Hz), 3.38 (3H, s); $\delta_C$ NMR (CDCl$_3$, 125.8 MHz)/ppm; 188.71 (CH), 161.55 (q), 152.43 (CH), 137.57 (CH), 131.75 (q), 94.07 (q), 89.19 (q), 75,56 (CH2), 71.90 (CH2), 70.79 (CH2), 70.06 (CH2), 59.13 (CH3).

Example 16: Synthesis of 3-Hydroxy-2,4,6-Triiodobenzaldehyde

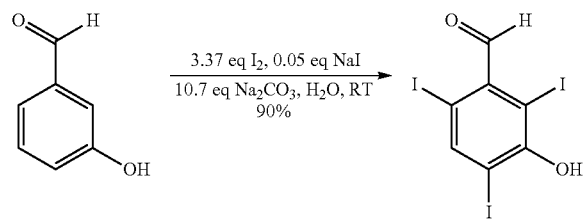 [SMILES: O=Cc1cccc(O)c1 ; O=Cc1c(I)cc(I)c(O)c1I]

To a 2L 3-necked rbf with large oval stirrer bar was added 3-hydroxybenzaldehyde (10.007 g, 81.89 mmol), sodium iodide (0.614 g, 4.09 mmol, 0.05 eq) and sodium carbonate (93.028 g, 877.44 mmol, 10.7 eq), rinsed in with a total of 750 ml of DI water. When the benzaldehyde had dissolved to give a bright yellow stirred solution, iodine balls (70.008 g, 275.80 mmol, 3.37 eq) was added in 2 portions over 30 minutes rinsed in with 225 ml of water each time. The reaction is followed by TLC (60% DCM in i-hex) and over 3 h, the iodine almost completely dissolves resulting in a dark yellow/orange precipitate. The solid was isolated by Büchner filtration and washed with i-hexane to remove any residual iodine. The isolated solid was re-dissolved in warm water (2L, 45° C.) to give a clear brown solution to which 100 ml of sat. sodium thiosulfate solution were added to reduce any remaining iodine. The pH of the solution was cautiously reduced from 10.2 to 3.26 using 1M HCl (care due to evolution of CO$_2$). The solid was isolated by filtration, washed with water (2×500 ml) and dried in a high vacuum oven at 30° C. to give the desired compound as a yellow solid (37.002 g, 90.3% yield, 97.2% HPLC purity); $\delta_H$ (CDCl$_3$, 500.1 MHz)/ppm; 9.65 (1H, s), 8.35 (1H, s), 6.42 (1H, s); $\delta_C$ NMR (CDCl$_3$, 125.8 MHz)/ppm; 194.90 (CH), 155.12 (q), 149.77 (CH), 135.69 (q), 88.78 (q), 87.66 (q), 85.70 (q).

Example 17: Synthesis of 2,4,6-Triiodo-3-(2-(2-Methoxyethoxy)Ethoxy)Benz Aldehyde

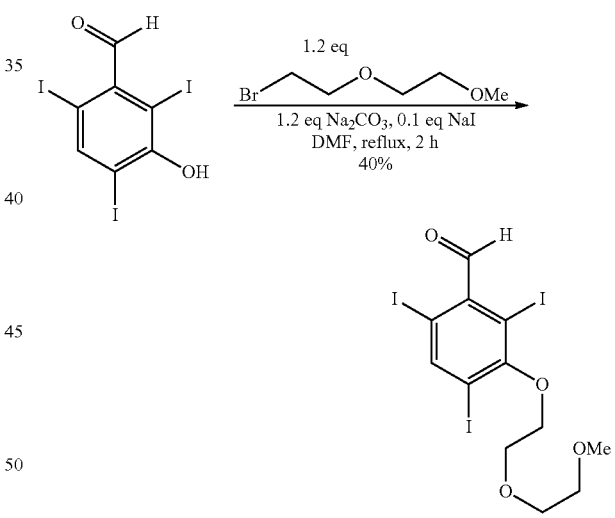

To a flame dried 250 ml 3-necked rbf under a nitrogen atmosphere containing a stir bar and fitted with a reflux condenser, were added 3-hydroxy-2,4,6-triiodobenzaldehyde (15.627 g, 31.3 mmol, 1.0 eq), sodium iodide (469 mg, 3.13 mmol, 0.1 eq), anhydrous sodium carbonate (3.981 g, 37.6 mmol, 1.2 eq) and anhydrous DMF (160 ml). The suspension was stirred until the aldehyde had completely dissolved, then 1-bromo-2-(2-methoxyethoxy)ethane (6.87 g, 37.5 mmol, 1.2 eq) was added by syringe and the reaction heated to reflux. After 2 h, TLC analysis (10% EA in i-hex) indicated the SM was consumed and the reaction was cooled to RT, transferred to a 250 ml rbf and evaporated to dryness under high vacuum. The resulting suspension was diluted with 500 ml of ethyl acetate, washed with 3×100 ml 1M NaOH, 2×100 ml sat. brine, decolourised with activated charcoal and dried with magnesium sulfate. The resulting solution was concentrated to dryness, and purified by silica column chromatography (2-20% ethyl acetate in i-hexane) and dried under high vacuum to give the desired compound as a yellow powder (7.556 g, 40.1%); $\delta_H$ (CDCl$_3$, 500.1 MHz)/ppm; 9.65 (1H, s), 8.44 (1H, s), 4.20 (2H, t, 6.4 Hz), 4.01 (2H, t, 6.4 Hz), 3.79 (2H, app. t, 5.8 Hz), 3.60 (2H, app. t, 5.8 H), 3.41 (3H, s); $\delta_C$ NMR (CDCl$_3$, 125.8 MHz)/ppm; 194.97 (CH), 159.10 (q), 150.83 (CH), 138.27 (q), 97.06 (q), 95.70 (q), 90.40 (q), 72.47 (CH2), 72.04 (CH2), 70.89 (CH2), 68.89 (CH2), 59.19 (CH3).

Example 18: Synthesis of 2,4,6-Triiodo-3-(2-(2-(2-Methoxyethoxy)Ethoxy) Ethoxy)Benz Aldehyde

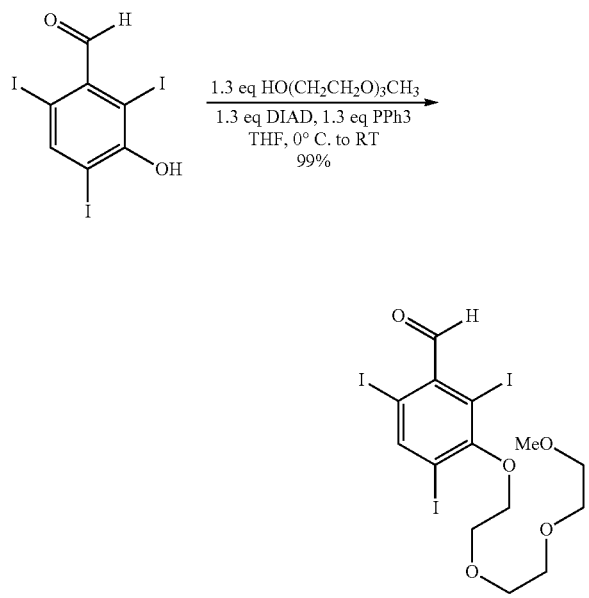

To a flame dried 100 ml 3-necked rbf containing a stirrer under a nitrogen blanket, was added triphenylphosphine (1.7216 g, 6.502 mmol, 1.3 eq) and anhydrous THF (35 ml). The stirring was started and, after full dissolution of the PPh3, the reactor was cooled to ca 0° C. in an ice-bath. To the colourless solution was added DIAD (1.28 ml, 6.502 mmol, 1.3 eq) dropwise via syringe resulting in a persistent yellow solution. After stirring for 5 minutes, triethylene glycol monomethyl ether (1.04 ml, 6.502 mmol, 1.3 eq) was added dropwise by syringe. After stirring for a further 5 minutes, the 3-hydroxy-2,4,6-triiodobenzaldehyde (2.5077 g, 5.002 mmol, 1.0 eq) was added in one portion resulting in an immediate colour change. The reaction was monitored by TLC (5% Et$_2$O in toluene) and left to stir overnight. The solution was diluted with ether to precipitate triphenylphosphine oxide and then concentrated to dryness. The resulting thick oil was purified by column chromatography (2-10% Et$_2$O in toluene) to give, after concentration and high vacuum drying, the desired product as a yellow powder (3.2077 g, 99% yield, 94.4% HPLC purity); $\delta_H$ (DMSO-D$_6$, 500.1 MHz)/ppm; 9.58 (1H, s), 8.47 (1H, s), 4.08 (2H, t, 4.9 Hz), 3.57-3.53 (4H, m), 3.44 (2H, app. t, 4.8 Hz), 3.24 (3H, s).

Example 19: Synthesis of 3,4,5-Triiodosalicylaldehyde

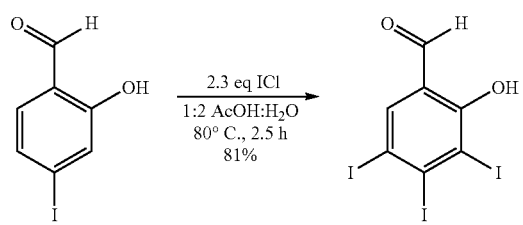 [SMILES: O=Cc1ccc(I)cc1O ; O=Cc1cc(I)c(I)c(I)c1O]

To a 3-necked 2L rbf containing a large oval stirrer was added 4-iodo-salicilaldehyde (25.01 g, 100.86 mmol, 1.0 eq) and acetic acid (300 ml). After stirring for 5 mins to allow the solid to dissolve, pre-warmed liquid iodine monochloride (39.11 g, 2.4 eq) was diluted with AcOH (100 ml) and transferred to a dropping funnel on the rbf. This solution was added over 10 mins. The reactor was then placed in a large silicone oil batch a fitted with a 1L dropping funnel, thermometer and condenser and set to heat to 80° C. During the heat up, water (700 ml) was slowly added to the solution causing a yellow/orange precipitation. After 20 mins at 80° C., the heating was turned off. After a further the heating bath was removed and the black solution/yellow suspension allowed to cool to RT and stir for 65 h; the reaction was analysed by TLC (20% EA in iHex). The solid was isolated by Büchner filtration and washed with water (2×500 ml). To remove residual iodine crystals, the solid was repeatedly re-slurried with i-hexane (200 ml) until the i-hexane supernatant was no longer purple. The isolated solid was dried in a hi-vac oven overnight to give the desired product as a yellow crystalline solid (40.84 g, 81% yield, 93.2% pure by HPLC analysis). The product could be further recrystallised to higher purity from acetone:water (9:1); $\delta_H$ (CDCl$_3$, 500.1 MHz)/ppm; 12.15 (1H, s), 9.67 (1H, s), 8.09 (1H, s); $\delta_C$ NMR (CDCl$_3$, 125.8 MHz)/ppm; 194.53 (CH), 159.58 (C), 142.24 (CH), 133.39 (C), 120.87 (C), 101.68 (C), 94.02 (C).

Example 20: Synthesis of 3,4,5-Triiodo-2-(2-(2-Methoxyethoxy)Ethoxy) Benzaldehyde

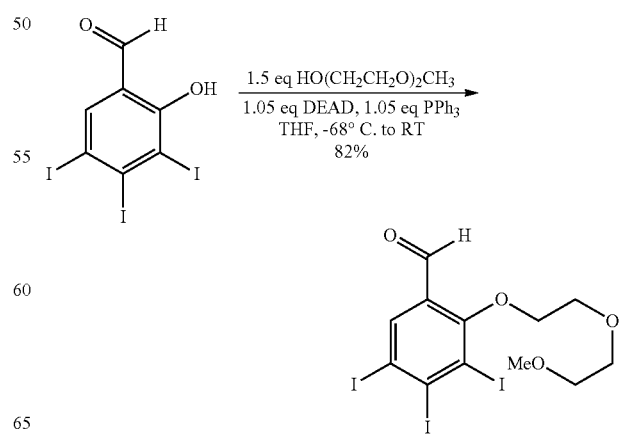

(5 g scale): To a flame dried 3-necked 250 ml rbf containing a small octagonal stirrer bar under a positive pressure of nitrogen, was added triphenylphosphine (2.76 g, 10.5 mmol, 1.05 eq) and dry THF (70 ml) by syringe. The rbf was placed in a Dewer bath fitted with a low temperature thermometer and cooled to −68° C. with an EtOH/liquid nitrogen bath. Diethyl azodicarboxylate (1.65 ml, 10.5 mmol, 1.05 eq) was added dropwise by syringe over 1 min and left to stir for 5 mins to give a yellow suspension. Diethyleneglycol mono-methyl ether (1.77 ml, 15 mmol, 1.5 eq) was then added dropwise and left to stir for 5 mins. To this was added solid 3,4,5-triiodosalicylaldehyde (5.00 g, 10.0 mmol, 1.0 eq) in one portion. The initial dark orange/red suspension lightened to give a pale yellow solution which was allowed to stir for 2 h, monitored by TLC analysis (20% ether in toluene) and left to warm up to RT O/N. TLC indicated complete consumption of aldehyde starting material with a clean reaction profile. The resulting solution was transferred to a 500 ml rbf, diluted with ether (200 ml) and cooled in the freezer. The resulting suspension was filtered through a short silica plug to remove triphenylphosphine oxide and flushed with further ether (200 ml). The resulting solution was concentrated to dryness, and purified by column chromatography eluting with ether in toluene (2-20%) with product fractions concentrated to dryness and dried under high vacuum to give the desired product as a yellow amorphous solid (4.91 g, 82% yield, 96% HPLC purity); $\delta_H$ (CDCl$_3$, 500.1 MHz)/ppm; 10.26 (1H, s), 8.34 (1H, s), 4.22 (2H, t, 4.5 Hz), 3.90 (2H, t, 4.5 Hz), 3.90 (2H, t, 4.6 Hz), 3.55 (2H, t, 4.6 Hz), 3.38 (3H, s); $\delta_C$ NMR (CDCl$_3$, 125.8 MHz)/ppm;

Example 21. Biodegradable Polymers with Ether Bonded Carboxylic Acid Drug Binding Species 1.0 g of PVA powder (10 kDa) is dissolved into 35 mL of 1-methyl-2-pyrrolidinone at 90° C. The temperature is then lowered to 50° C., followed by addition of 3-bromopropionic acid (0.42 g, 2.7 mmol) and sodium hydroxide powder (0.22 g, 5.4 mmol.). Reaction temperature is maintained at 50° C. and stirring continues at 350 rpm overnight. After the reaction has stopped, the solution is added dropwise into acetone (200 ml) to precipitate out the polymer. The polymer solid is then washed with methanol (100 ml) to remove the sodium hydroxide and the polymer dried under vacuum (24 hours). Following Example 1, biodegradable beads are then synthesized using the functionalized PVA polymer.

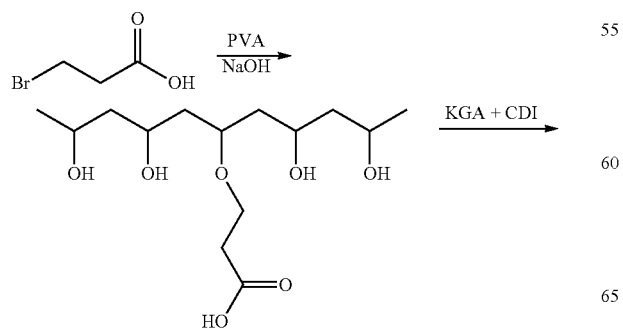

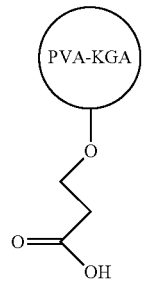

Example 22. Biodegradable Polymers with Ester Bonded Radiopaque Groups 2,3,5-Triiodobenzoic acid (5 g, 10 mmol) is dissolved in 25 ml NMP in a 100 mL three necked round bottom flask. Thionyl chloride (1.3 g, 11 mmol) is diluted into 5 ml NMP solution and added into the reaction vessel. The reaction mixture is heated to 70° C. for 3 hours. After reaction, the solution is placed onto a rotary evaporator to remove excess thionyl chloride and gas by products.

1.0 g of PVA powder (10 kDa) is dissolved into 35 mL of 1-methyl-2-pyrrolidinone at 90° C. The temperature is then lowered to 50° C., followed by addition of the 2,3,5-triiodobenzoic chloride intermediate solution (7 ml, 2.3 mmol) to the PVA solution along with the triethylamine catalyst solution (1 ml). The reaction is stirred at 350 rpm overnight. After the reaction was stopped, the solution is added dropwise into acetone (200 ml) to precipitate out the polymer. This polymer is then re-dissolved in NMP and precipitated into acetone again to purify the polymer. The polymer is then dried under vacuum (24 hours). Following Example 1, biodegradable beads are then synthesized using the functionalized PVA polymer.

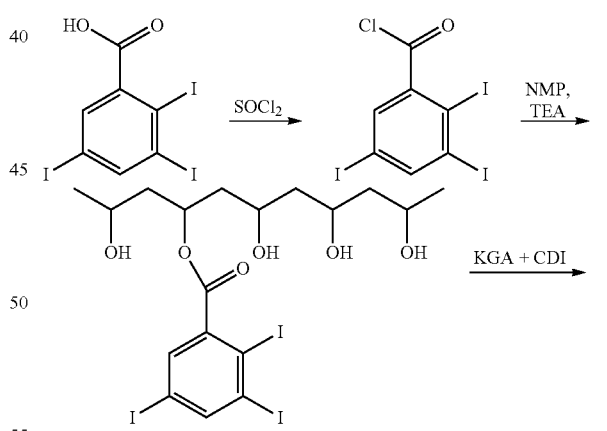

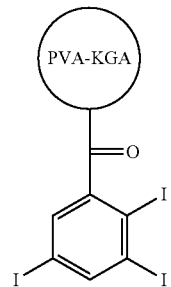

Example 23: Drug Loading of Modified Microspheres 1 mL of microspheres from examples 9, 10, 11 and 12 were suspended in 1.5 mL of doxorubicin solution (concentration 25 mg/mL) under constant agitation. At predetermined time points the supernatant solution was sampled and doxorubicin concentration determined at UV at 483 nm against a known reference.

The loading profiles are given in FIG. 4

The invention claimed is:

1. A polymer having a backbone comprising a polyhydroxylated polymer cross linked by a C4 or C5 alpha keto acid, wherein the cross linked polymer is in the form of a microsphere having a diameter between 30 µm and 700 µm when swollen.

2. The polymer according to claim 1, wherein the C4 or C5 alpha keto acid, preferably is alpha ketoglutarate.

3. The polymer according to claim 1, wherein the cross linking groups are of the formula 1:

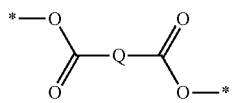   1 wherein

*is the point of attachment to the polyhydroxylated polymer; and wherein Q is a group of the formula 1a:

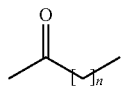   Ia wherein n is 1 or 2.

4. A polymer according to claim 1, wherein the polyhydroxylated polymer is or comprises PVA.

5. A polymer according to claim 1, wherein the polyhydroxylated polymer is or comprises PVA and comprises cross linking groups of formula 3 which cross link the PVA

   3 wherein

Q is a group of the formula 1a

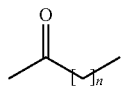   Ia wherein n is wherein n is 1 or 2.

6. A polymer according to claim 4, wherein the PVA has a weight average molecular weight of 2,000 Da to 180,000 Da.

7. A polymer according to claim 4, wherein the PVA has a weight average molecular weight of 10,000 Da to 32,000 Da.

8. A polymer according to claim 4, wherein the PVA has a weight average molecular weight of 2,000 Da to 32,000 Da.

9. A polymer according to claim 1, wherein the polymer is a hydrogel.

10. A polymer according to claim 1, wherein the polymer further comprises an imagable agent.

11. A polymer according to claim 1, wherein the polymer is ionically charged at pH7.4.

12. A polymer according to claim 1, wherein the polymer comprises a covalently bound ionic group which is ionized at pH 7.4.

13. A microparticle or microsphere comprising a polymer according to claim 1.

14. A microparticle or microsphere according to claim 13, for use in the embolization of a blood vessel.

15. A pharmaceutical composition comprising one or more microparticles or microspheres according to claim 13, and a pharmaceutically acceptable carrier or diluent.

* * * * *